US012133974B2

(12) United States Patent
Daftary et al.

(10) Patent No.: US 12,133,974 B2
(45) Date of Patent: Nov. 5, 2024

(54) SAFETY HOUSING BASED IMPLANT/MEDICAMENT INJECTING SYSTEM

(71) Applicant: BHARAT SERUMS AND VACCINES LTD, Maharashtra (IN)

(72) Inventors: Gautam Vinod Daftary, Mumbai (IN); Suresh Kumar Natarajan, Bangalore (IN); Vasanthan Mani, Bangalore (IN); Cyril Fernandez Lourdnathan Joseph, Wayanad (IN); Sangeeta Hanurmesh Rivankar, Mumbai (IN)

(73) Assignee: BHARAT SERUMS AND VACCINES LTD, Mumbai (IN)

( * ) Notice: Subject to any disclaimer, the term of this patent is extended or adjusted under 35 U.S.C. 154(b) by 193 days.

(21) Appl. No.: 17/583,976

(22) Filed: Jan. 25, 2022

(65) Prior Publication Data
US 2022/0143326 A1     May 12, 2022

Related U.S. Application Data

(62) Division of application No. 16/322,974, filed as application No. PCT/IN2016/000238 on Oct. 3, 2016, now Pat. No. 11,273,266.

(30) Foreign Application Priority Data

Aug. 5, 2016 (IN) .............................. 201621026847

(51) Int. Cl.
*A61M 5/32* (2006.01)
*A61M 5/315* (2006.01)
(Continued)

(52) U.S. Cl.
CPC ...... *A61M 5/3221* (2013.01); *A61M 5/31501* (2013.01); *A61M 5/31531* (2013.01);
(Continued)

(58) Field of Classification Search
CPC .............. A61M 5/178; A61M 5/31501; A61M 5/31505; A61M 5/31511; A61M 5/31515;
(Continued)

(56) References Cited

U.S. PATENT DOCUMENTS

| 4,747,829 A | 5/1988 | Jacob et al. |
| 4,969,877 A | 11/1990 | Kornberg |

(Continued)

FOREIGN PATENT DOCUMENTS

| EP | 0966983 | 12/1999 |
| WO | 2012/098356 | 7/2012 |

OTHER PUBLICATIONS

International Search Report issued in PCT/IN2016/000238 on May 23, 2017 (5 pages).

*Primary Examiner* — Kami A Bosworth
(74) *Attorney, Agent, or Firm* — MASUVALLEY & PARTNERS; Peter Martinez

(57) ABSTRACT

A safety housing based implant/medicament injecting system. The system includes a needle assembly prefilled with an implant/medicament for injection and an injecting needle/cannula, a housing for accommodating the needle assembly under usual bias inside said housing, a plunger means having a plunger rod configured for stage-wise forward motion including an initial-injecting plunger forward motion with the needle assembly within the housing to first engage the needle assembly with the housing and a subsequent continuing-injecting plunger forward motion independent of the needle assembly for injecting the implant/medicament. The needle assembly configured to return post-injecting to be secured inside said housing blocking any subsequent use thereof.

13 Claims, 20 Drawing Sheets

(51) Int. Cl.
*A61M 5/50* (2006.01)
*A61M 37/00* (2006.01)

(52) U.S. Cl.
CPC ........ *A61M 5/3234* (2013.01); *A61M 5/3243* (2013.01); *A61M 5/50* (2013.01); *A61M 37/0069* (2013.01); *A61M 2005/31508* (2013.01); *A61M 2005/3223* (2013.01); *A61M 2005/3231* (2013.01); *A61M 2005/3258* (2013.01); *A61M 2005/3261* (2013.01); *A61M 2005/3267* (2013.01); *A61M 2205/273* (2013.01); *A61M 2205/581* (2013.01)

(58) Field of Classification Search
CPC .......... A61M 5/31565; A61M 5/31566; A61M 5/31578; A61M 5/3158; A61M 5/31591; A61M 5/322; A61M 5/3221; A61M 5/3232; A61M 2005/31506; A61M 2005/3223; A61M 37/0069
See application file for complete search history.

(56) References Cited

U.S. PATENT DOCUMENTS

| | | |
|---|---|---|
| 5,201,719 A | 4/1993 | Collins et al. |
| 5,273,532 A | 12/1993 | Niezink et al. |
| 6,102,896 A | 8/2000 | Roser |
| 7,118,552 B2 | 10/2006 | Shaw et al. |
| 8,029,458 B2 | 10/2011 | Cherif-Cheikh et al. |
| 2002/0010421 A1 | 1/2002 | Buttgen et al. |
| 2002/0111603 A1 | 8/2002 | Cheikh |
| 2003/0004457 A1 | 1/2003 | Andersson |
| 2007/0129686 A1 | 6/2007 | Daily et al. |
| 2008/0221529 A1 | 9/2008 | Kiehne |
| 2012/0253314 A1 | 10/2012 | Harish et al. |
| 2014/0018725 A1 | 1/2014 | Potter et al. |
| 2019/0117903 A1 | 4/2019 | Rathore et al. |

Safety Clip Butt joint with Needle assembly

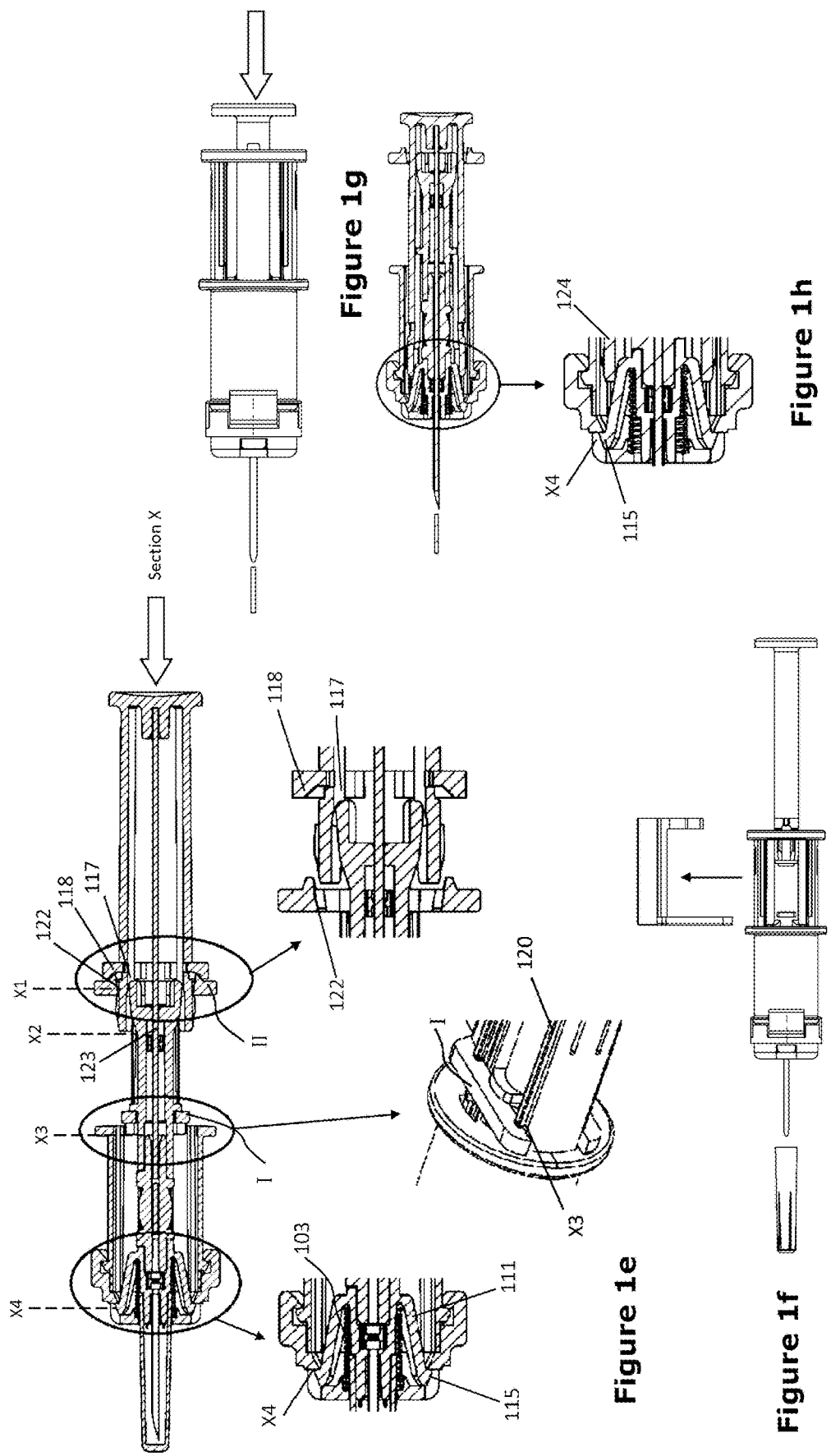

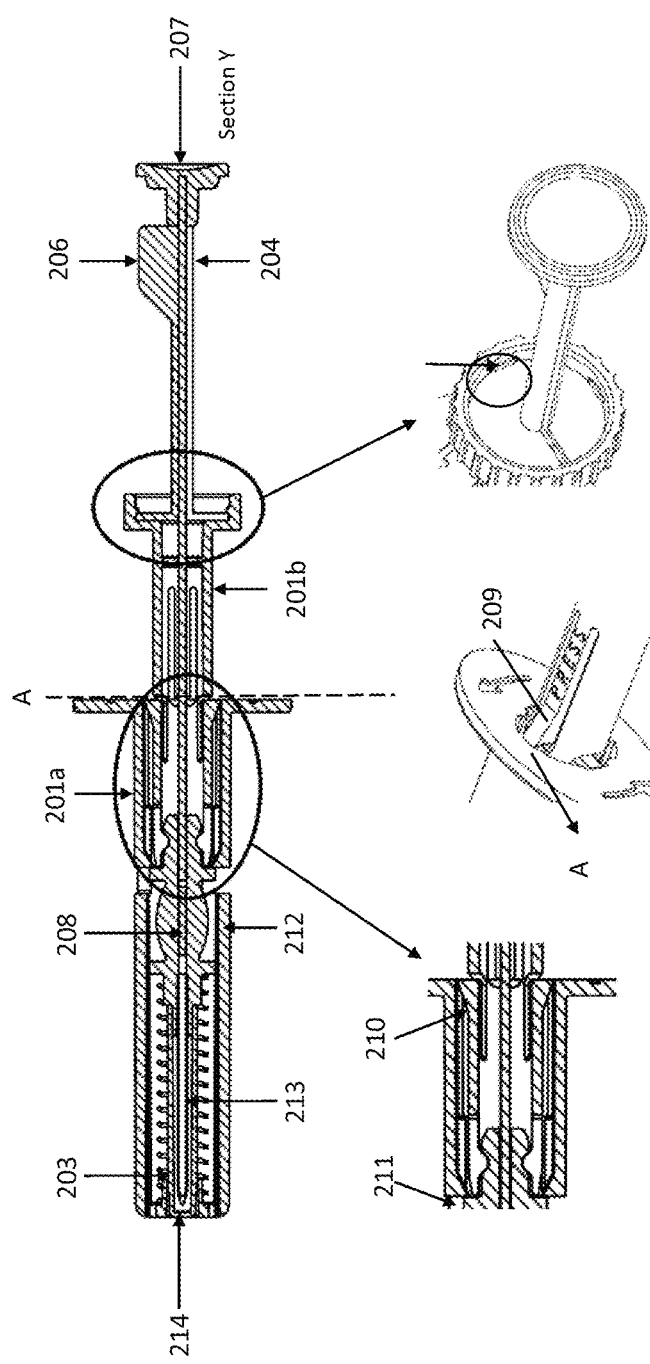
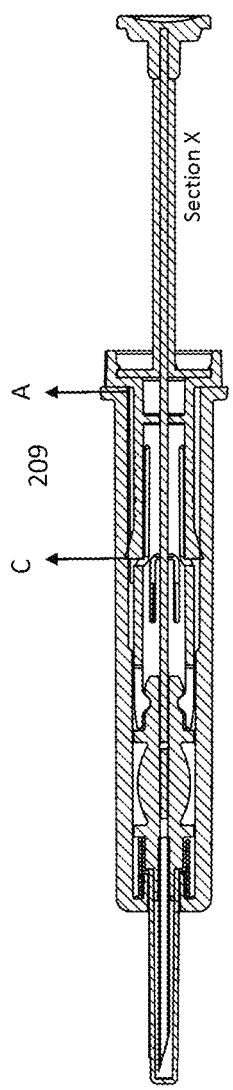
Figure 2c
Figure 2d

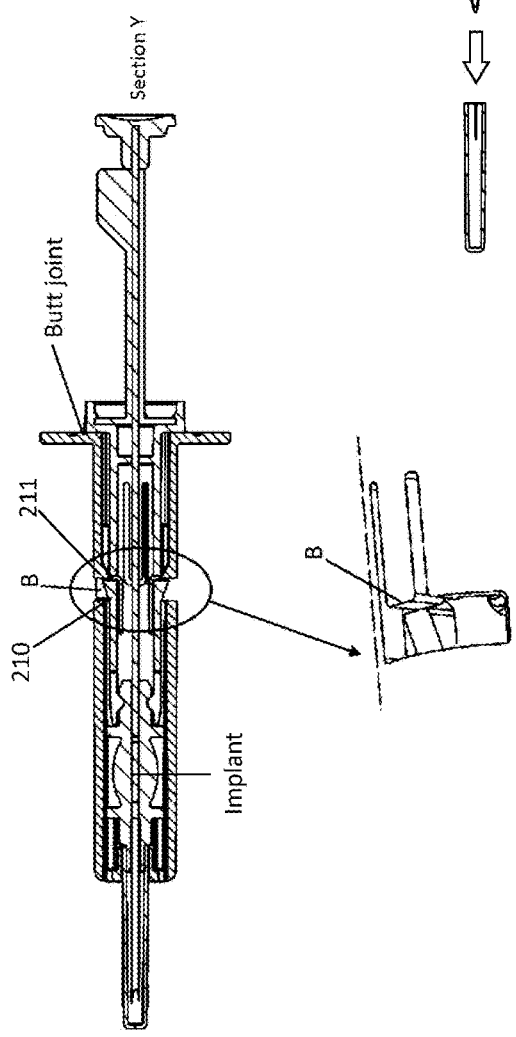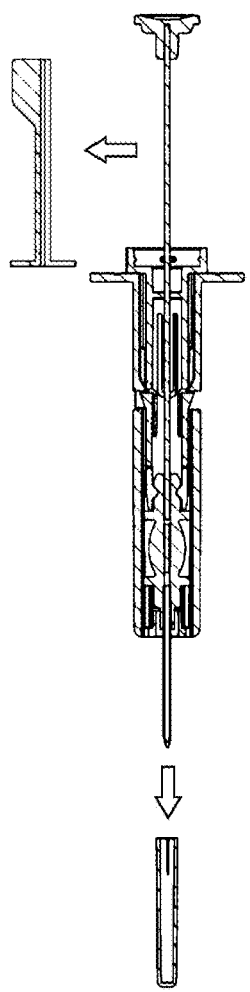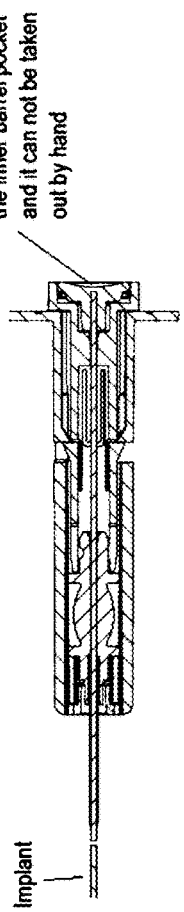
Figure 2e
Figure 2f
Figure 2g

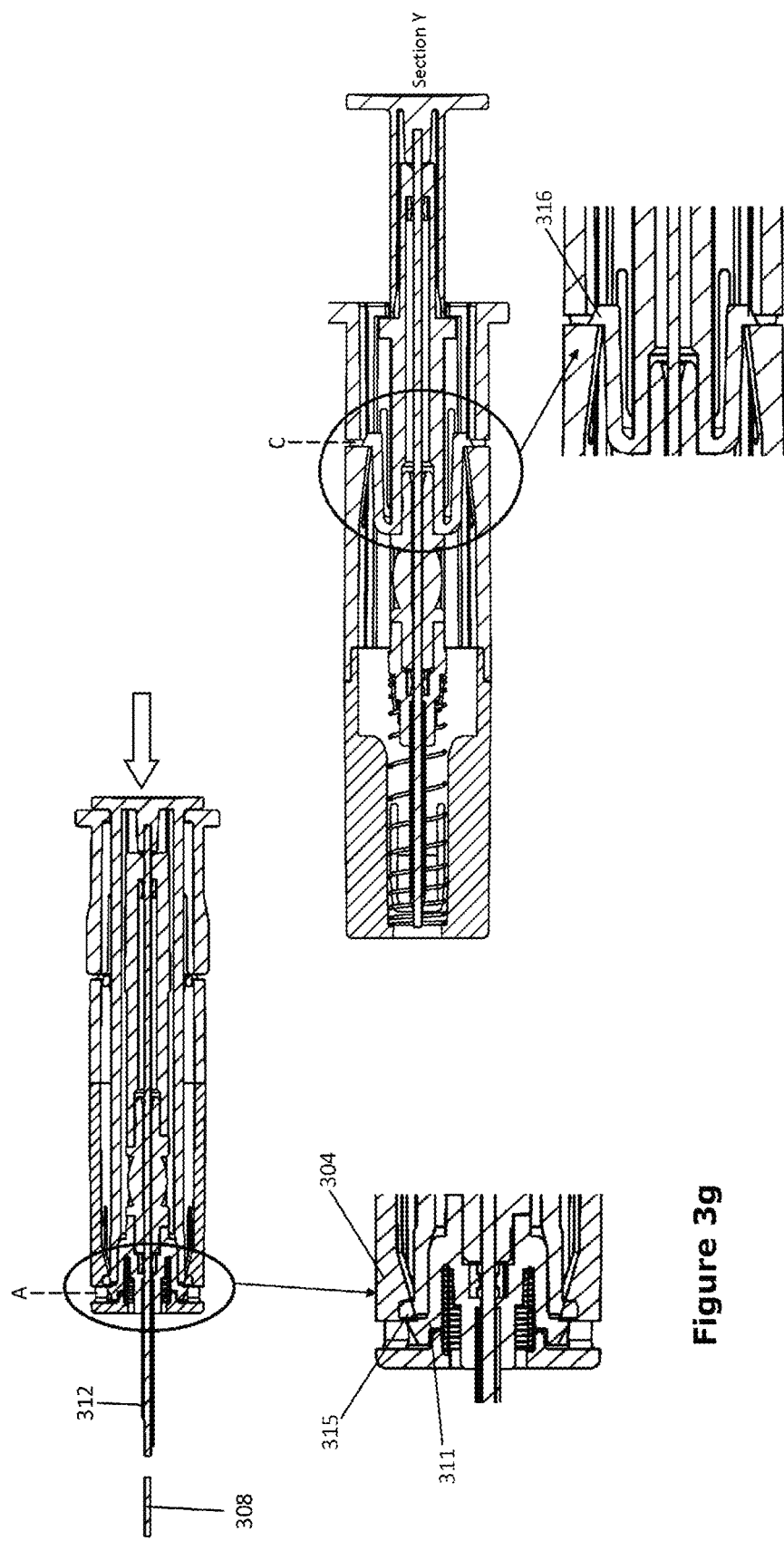

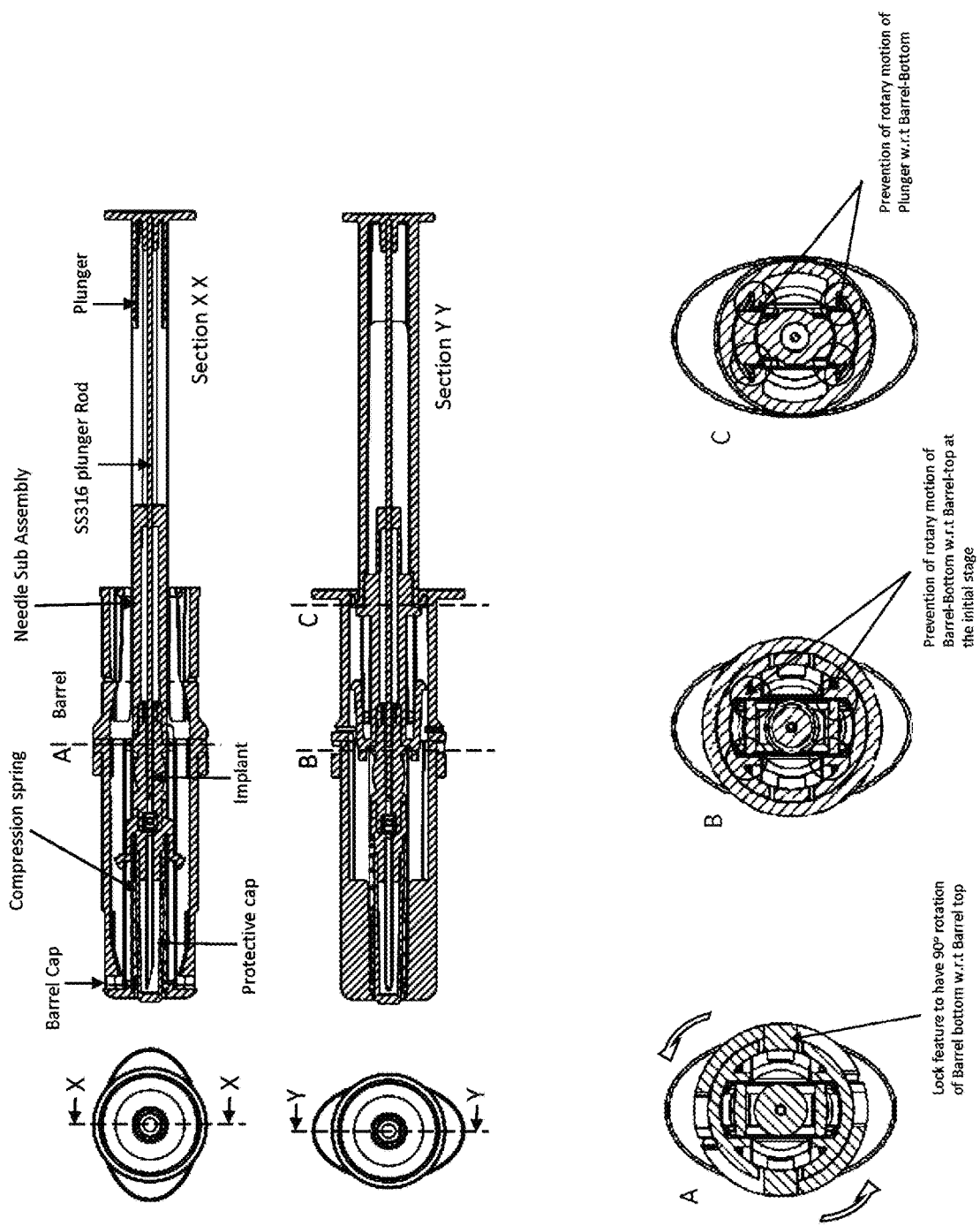

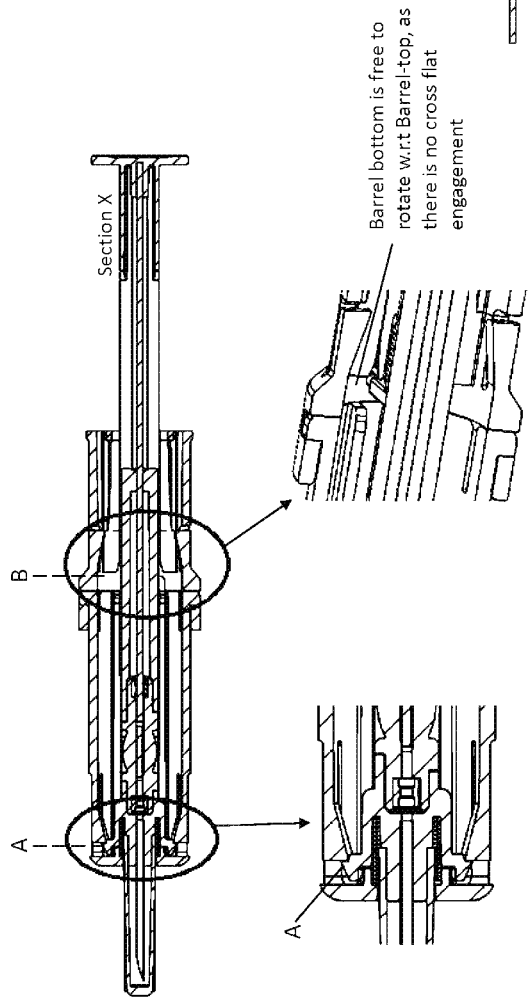
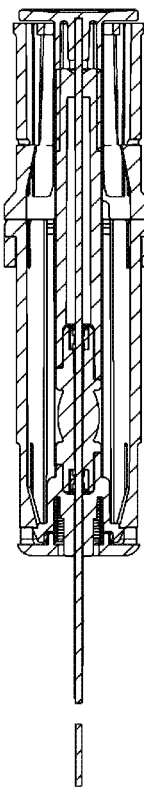
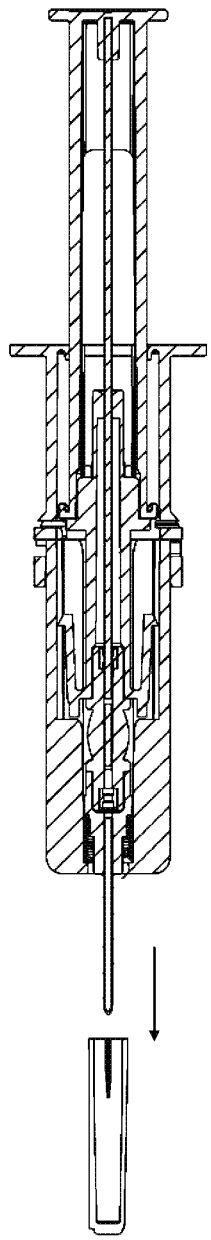
Figure 4e
Figure 4f
Figure 4g

SAFETY HOUSING BASED IMPLANT/MEDICAMENT INJECTING SYSTEM

RELATED APPLICATIONS

This application is a divisional of and claims priority to U.S. patent application Ser. No. 16/322,974, filed Feb. 4, 2019, which is a U.S. National Phase application under 35 U.S.C. § 371 of International Patent Application No. PCT/IN2016/000238, International Filing Date Oct. 3, 2016, which claims the benefit of India Patent Application No. 201621026847 filed Aug. 5, 2016; all of which are incorporated herein by reference in their entireties.

FILED OF THE INVENTION

The present invention relates to a system for safely injecting substances into body/tissue of human/animal. More particularly, the present invention is directed to provide a prefilled medicament injecting system with a safety housing for safely injecting substances like medicament/implant into the body or tissue of the human or the animal. The safety housing is specially configured to prevent any-contact between injecting needle and the user during the injecting procedure or in the post injecting stage.

BACKGROUND ART

A conventional medicament/implant injecting system includes an injecting syringe, which is filled with a selected dosage of the medicament/implant for distribution to the end use. The injecting system further includes a sharp-pointed element or injecting needle at front of the injecting syringe for piercing into the body/tissue and delivering the medicament of the injecting syringe.

Sometimes, the injecting needle of the injecting system causes needle stick injuries to the user who is using the injecting system to inject the medicament.

The needle stick injuries are common to the healthcare professionals and, in some cases, the needle stick injuries exposed the healthcare professionals to contamination from infected patients being injected.

In recent times, different safety shields for injecting systems have been reported in the art to avoid the needle stick injuries. These safety shields are adapted to move in axial direction with respect to the injecting syringe to expose the needle 'for use' only during injection of the medicament/implant. E.g.

EP 0966983 A1 discloses a shield system and a syringe which is coupled to the shield system. The shield system includes an outer syringe holder and an inner shield. The syringe is inserted within the enclosure defined by the outer holder and inner shield. When sufficient pressure is exerted on the holder by the syringe barrel, the shield is released and is urged in a distal direction by a spring located between the barrel and shield, putting the shield in an extended position and covering the needle.

U.S. Pat. No. 8,029,458 B2 discloses a device for the injection of a solid or semi-solid implant comprising of a main hollow body having a hollow needle fixed thereto, into which the implant is introduced; a secondary body which is disposed coaxially inside the main body and which surrounds the needle and a plunger rod which can slide coaxially inside the hollow needle. The injection device is arranged such that: (i) when it is pressed against the tissues, the main body slides along the length of the secondary body from a proximal position to a distal position such that the needle can penetrate the tissues, whereby the movement of the main body is accompanied by the concomitant movement of the plunger rod; and (ii) the plunger rod remains fixed and maintains the implant at the required depth in the tissues until the needle is removed therefrom when the main body is returned from the distal position to the proximal position.

U.S. Pat. No. 7,118,552 B2 discloses an automatically operable safety shield system for syringes which includes an inner holder into which the syringe may be inserted, an outer shield mounted outwards from the inner holder being biased with a spring and axially movable relative to the inner holder between retracted and extended positions wherein in the retracted position of the outer shield the syringe needle is exposed for use. The inner holder comprises at least one first opening and the outer shield comprises at least one first stop member, the first stop member being engageable with the first opening when the outer shield is in the retracted position, the inner holder having distal to the first opening at least one first indentation, the first stop member being engageable with the first indentation when the outer shield is in the extended position. A trigger is positioned within the inner holder and axially movable relative to said inner holder such that it can contact the first stop member when it is engaged with the first opening and disengage the first stop member from the first opening, allowing the spring to move the outer shield to the extended position.

Safety shield systems or the safety housings for injecting system such as mentioned in both the U.S. Pat. No. 8,029,458 B2 and U.S. Pat. No. 7,118,552 B2 include an inner housing to enclose the injecting syringes and an outer housing to accommodate the inner housing wherein the outer housing moves to expose the injecting syringes and goes back to its original position post injection. Now this two part housing structures based covering and selective exposure of the injecting syringe with the assistance of a trigger mechanism makes the whole arrangement complex and difficult to use, for health professional as the outer hosing needs to be moved separately before injecting and thus continuing to expose the user to accidental hazards.

The above state of art clearly indicates that, there has been a need for developing a simple, easy-to-use, safety housing for injecting system which can prevent any contact between injecting needle and the user during the injecting procedure or in the post injecting stage to avoid the needle stick injuries.

OBJECTS OF THE INVENTION

The basic object of the present invention is to develop a simple, user friendly safety shield system or the safety housing for medicament/implant injecting system which would expose the injecting needle, only during injecting procedure and automatically enclose the injecting needle in post injection stage such as to avoid the needle stick injuries.

Another object of the present invention is to develop a safety housing for medicament/implant injecting system which will be adapted to permanently enclose injecting unit post use for restricting any further use of the injecting unit and/or accidental exposure of the used needle.

SUMMARY OF THE INVENTION

According an aspect in the present invention there is provided another preferred embodiment of the present safety housing based implant/medicament injecting system which is twist based safety housing based implant/medicament injecting system comprising of
- a housing comprising an outer housing and an inner housing;
- a needle assembly having a cannula at a front end of the needle assembly and a subsequent needle holder that is in fluid communicable connection with the cannula, the needle holder being fully accommodated within the inner housing and the outer housing and supported with an expanded spring positioned between an outer housing top and the front end of the needle assembly;
- a plunger rod configured for:
- an initial forward motion of the plunger rod to eject the cannula through an opening in the outer housing.
- wherein a releasable seal means operatively couples the plunger rod with a back end of the needle assembly and with the inner housing, and wherein a first engagement means to engage the needle assembly with the outer housing at an end of the initial forward motion of the plunger rod; and
- a subsequent continuing forward motion of the plunger rod to inject an implant/medicament through the ejected cannula, wherein a seal releasing means disengages the coupling between needle assembly, the inner housing and the plunger rod;
- a first disengagement means for disengaging the first engagement means; and
- a second engagement means on the needle holder to permanently arrest the needle assembly in the housing after use.

In above mentioned twist based safety housing based implant/medicament injecting system, the outer housing is configured to fully enclose the needle assembly, the inner housing is coupled to a back end of the outer housing and is configured to telescopically move within the outer housing and
  said inner housing surrounds a coupling point between the plunger rod and the back end of the needle assembly.

In above mentioned twist based safety housing based implant/medicament injecting system, the plunger rod includes a plunger cap at a back end of the plunger rod.

In above mentioned twist based safety housing based implant/medicament injecting system, the inner housing comprises a reverse snap seated inside a groove of the outer housing to arrest any rotation of the inner housing during the ejection of the cannula from the outer housing.

In above mentioned twist based safety housing based implant/medicament injecting system, the releasable seal means involves a safety cap provided on the plunger rod and providing a butt joint with the inner housing;
  wherein the safety cap ensures that the plunger rod cooperatively move with the inner housing and the needle assembly and that any pushing force applied on the plunger cap gets transferred to the inner housing and the needle assembly via the safety cap so that the needle assembly, which is surrounded with the inner housing, is driven in a forward direction through the outer housing; and
  wherein said cooperative movement of the plunger rod with the inner housing and the needle assembly restricts plunger rod movement through the needle holder and thus prevents movement of the implant/medicament independently with respect to the needle assembly during the initial forward motion of the plunger rod.

In above mentioned twist based safety housing based implant/medicament injecting system, the inner housing includes a forward snap configured to be released by pressing, such release causing the inner housing to be driven into the outer housing to eject the cannula out of the outer housing during the initial forward motion of the plunger rod.

In above mentioned twist based safety housing based implant/medicament injecting system, the needle assembly includes a protective cap on the cannula;
  wherein the first engagement means includes a reverse snap on the inner housing and a forward snap lock in the outer housing;
  wherein, during the initial forward motion of the plunger rod, force is applied on the plunger cap to drive the needle assembly and the inner housing within the outer housing towards the opening in the outer housing; and
  wherein, said reverse snap on the inner housing get snap locked with the forward snap lock in the outer housing when the cannula and the protective cap are completely ejected through the opening in the outer housing.

In above mentioned twist based safety housing based implant/medicament injecting system, the reverse snap on the inner housing getting snap-locked with the forward snap lock in the outer housing causes an audible click sound and causes the spring to be compressed to arrest reverse movement of the needle assembly with respect to the housing.

In above mentioned twist based safety housing based implant/medicament injecting system, forward movement of the needle assembly when the cannula is completely ejected through the opening in the outer housing is arrested by having a butt joint between the inner housing and the outer housing, and wherein the cannula being completely ejected through the opening allows for the cannula, after removal of the protective cap, to pierce a body, skin or tissue.

In above mentioned twist based safety housing based implant/medicament injecting system, the seal releasing means is in a back end of the inner housing and is a safety cap that can be removed to enable the plunger rod to move independent of the needle assembly when a pushing force is applied on the plunger cap so that the subsequent continuing forward motion of the plunger rod causes the plunger rod to travel a forward direction through the needle holder and push the implant/medicament through the cannula into tissue.

In above mentioned twist based safety housing based implant/medicament injecting system, at an end of the injection of the implant/medicament, the plunger cap irrecoverably sits within an inner housing pocket.

In above mentioned twist based safety housing based implant/medicament injecting system, the first disengagement includes a circular snap between the needle assembly and the outer housing;
  wherein said circular snap enables integrated rotation of the inner housing, the plunger rod and the plunger cap with rotation of a grip area on the inner housing and arrest rotation of the needle assembly;
  wherein said rotation of the inner housing, the plunger rod and the plunger cap disengages the snap-lock between the reverse snap on the inner housing and the forward snap lock in the outer housing; and
  wherein, after the first engagement means is disengaged, the needle assembly automatically retracts within the housing by expansion of the spring.

In above mentioned twist based safety housing based implant/medicament injecting system, the second engagement means includes a lock between the needle holder and the forward snap lock to permanently arrest the needle assembly in the outer housing after use.

BRIEF DESCRIPTION OF THE ACCOMPANYING DRAWINGS

FIG. 1a-1i illustrates a preferred embodiment of the present safety housing based implant/medicament injecting system which is a push type safety housing based implant/medicament injecting system.

FIG. 2a-2i illustrates a preferred embodiment of the present safety housing based implant/medicament injecting system which is a twist type safety housing based implant/medicament injecting system.

FIG. 3a-3h illustrates a preferred embodiment of the present safety housing based implant/medicament injecting system which is a press type safety housing based implant/medicament injecting system.

FIG. 4a-4h illustrates a preferred embodiment of the present safety housing based implant/medicament injecting system which is a hybrid type safety housing based implant/medicament injecting system.

Figure 1A:
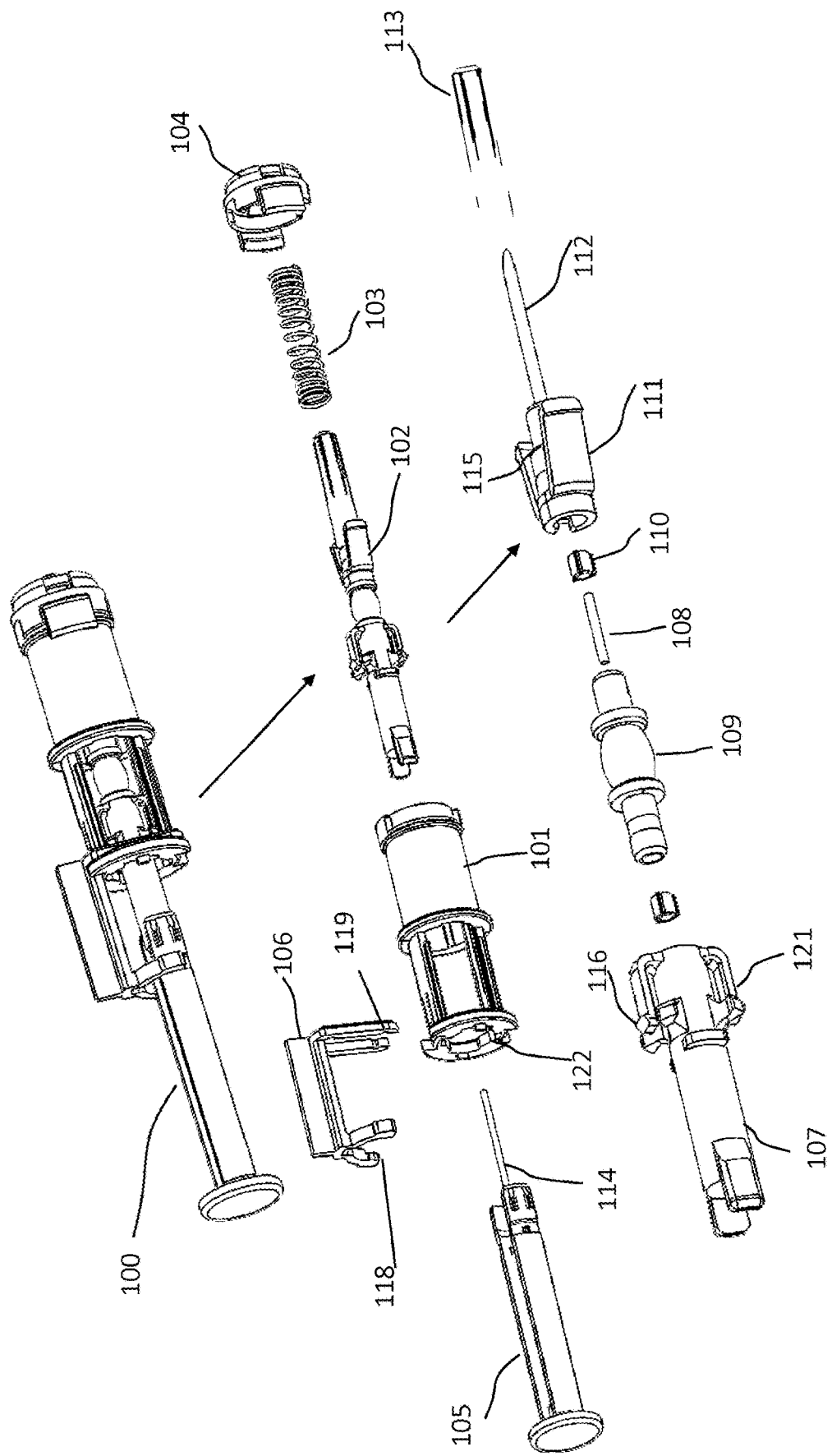

DETAILED DESCRIPTION OF THE INVENTION WITH REFERENCE TO THE ACCOMPANYING DRAWINGS

The present invention discloses a safety housing based implant/medicament injecting system for safely introducing implant/medicament or injectable substances into body/tissue of human/animal for medical or physical purposes.

The present injecting system includes a housing and an injecting syringe or needle assembly with an injecting needle/cannula. The injecting syringe or needle assembly is pre-filled with injectable substances or medicament/implant. The housing is configured to fully accommodates the needle assembly.

The housing includes a small opening at its front end. The needle assembly is fully enclosed within said housing and provided therein under support of a spring from a front end of the housing in such a manner that, the cannula, which is positioned at front end of the needle assembly, can be ejected through said front opening of the housing for piercing skin, body tissue and deliver the implant/medicament.

The injecting system also includes a plunger means. The plunger means includes a plunger rod. The plunger rod is concentrically disposed with respect to the housing, at back end of the housing and coupled with the needle assembly.

The plunger means is configured for an initial injecting plunger forward motion coupled with the needle assembly to expose the needle/cannula through the front opening of the housing and engage the needle assembly with the housing to keep the needle/cannula exposed for injection. The operative coupling between the plunger means and the needle assembly gets released at the end of the initial injecting plunger forward motion. This enables the plunger means for a subsequent continuing injecting plunger forward motion. The plunger rod enter in the needle assembly during the subsequent continuing injecting plunger forward motion to inject the implant/medicament through the exposed needle/cannula.

In the present injecting system, the plunger means is coupled with the needle assembly by a releasable seal means during the initial injecting plunger forward motion. This coupling ensures transferring of a pushing force applied on the plunger means to the needle assembly and co-forward movement of the plunger means and the needle assembly inside the housing by compressing the spring until a first engagement means engages the needle assembly with the front end of the housing. In this engaged condition, the cannula is completely ejected through the front opening and any forward or backward motion of the needle assembly is arrested.

The plunger means, for its subsequent continuing injecting plunger forward motion, is decoupled from the needle assembly by a seal releasing means. The seal releasing means is configured to open the releasable seal means to decouple the plunger means from the needle assembly. The decoupling of the plunger means from the needle assembly enables independent forward movement of the plunger means inside the housing upon continuing application of the pushing force on the plunger means. This independent forward movement of the plunger means causes forward movement of the plunger rod in the needle assembly for pushing the implant/medicament through the cannula into the tissue.

The present safety housing based implant/medicament injecting system also includes a first disengagement means. The first disengagement means is configured to disengage the first engagement means upon completing delivery of the implant/medicament and thereby enable the automatic retraction of the needle assembly with the cannula in the housing under bias of the spring. The retracted needle assembly is locked within the housing with the help of a second engagement means. This avoids any future use/accidental exposure of the used needle/cannula.

In a preferred embodiment of the present safety housing based implant/medicament injecting system, the injecting needle/cannula may be covered with a removable protective cap. The inner surface of the housing and outer surface of the needle assembly includes cooperative guiding means to arrest any unwanted rotation of the needle assembly within the housing. Also, the needle assembly may includes forward snap which sits within the housing and configured to freely move in the forward direction inside the housing to prevent any accidental reverse movement of the needle assembly.

Figure 1B:
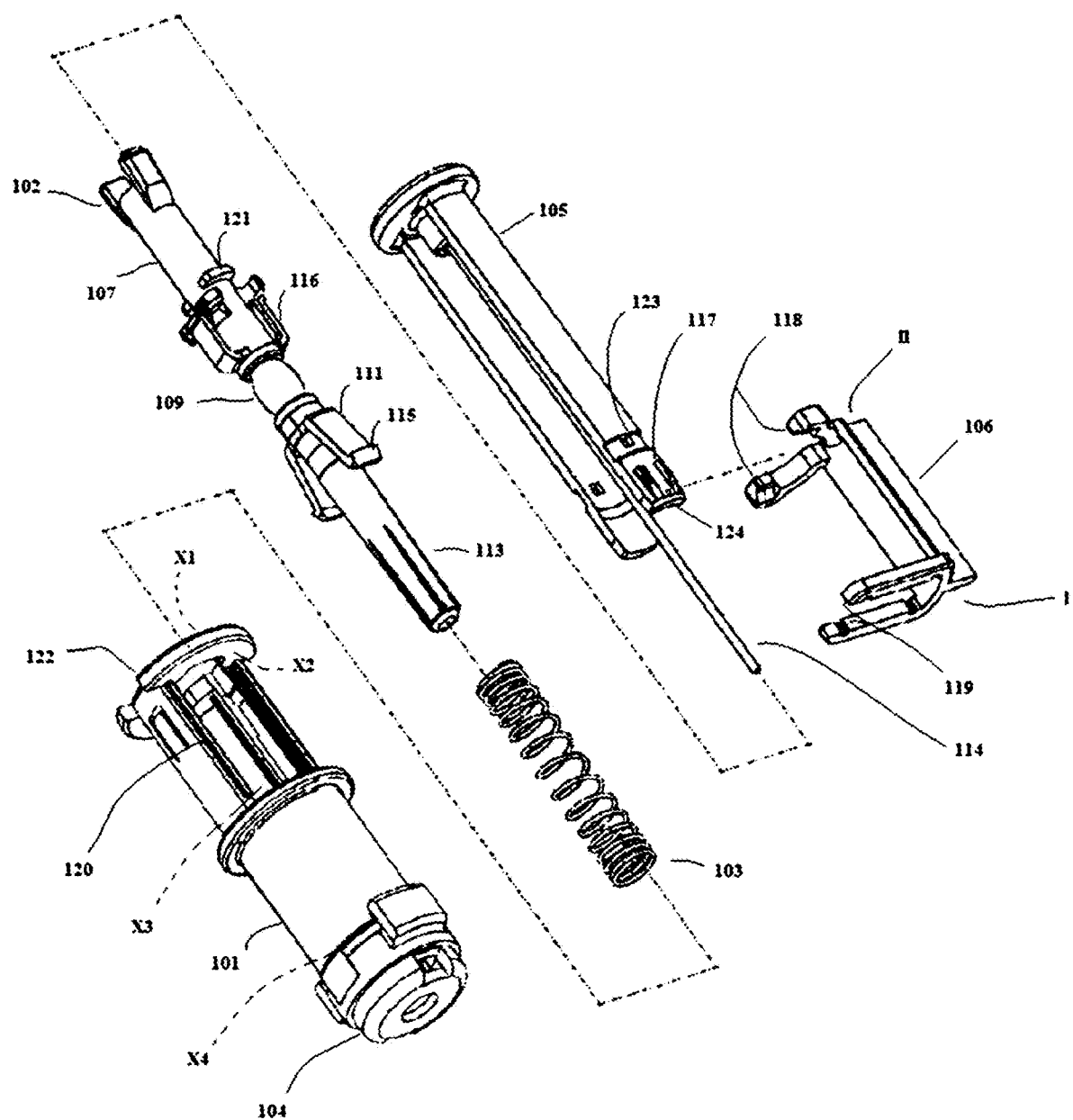

Reference is first invited from the accompanying FIGS. 1a and 1b which shows the present injecting system embodiment with push type safety housing. As shown in the referred figures, the push based pre-filled medicament injecting device 100 includes a needle assembly 102 which is fully enclosed within a housing 101. The housing 100 is preferably a cylindrical barrel. The needle assembly 102 is secured within the housing 101 and supported a spring 103 from the housing front top or cap 104.

Back end of the needle assembly 102 is coupled with a plunger 105 and a plunger rod 114 is insert molded within the plunger. The coupling between the needle assembly 102 and the plunger 105 is further supported with a safety clip 106.

The needle assembly 102 includes a label holder 107 at its back end. A plunger rod guide 110 which runs through implant magnifier cum container 109 is positioned between the label holder 107 and a needle hub 111. The plunger rod 114 can moves through the plunger rod guide 110 and pushes implant or the injectable substances 108 in the implant container 109 towards the needle hub 111. The needle hub 111 houses a cannula 112 which is having a fluid communicable connection with the plunger rod guide 110 to receive the implant or the injectable substances 108. The cannula 112 is adapted to eject through the small opening 104a defined in the housing top 104 and penetrates within the body or tissue and delivers the implant or the injectable substances 108. A protective cap 113 is provided on the cannula 112.

The needle hub 111 is coupled with inner surface of the housing 101 by a tongue and groove joint. This coupling arrests any rotational movement of the needle assembly 102 in the housing 101 and allows only spring biased forward and backward motion of the needle assembly 102 within the housing 101. The needle hub 111 also includes a snap lock 115 which is configured to engage with cooperative locking portion in the housing front top or cap 104. The snap lock 115 of the needle hub 111 with cooperative locking portion in the housing top 104 constitutes the first engagement means of the present embodiment.

The label holder 107 includes a snap 116 which sits within the barrel 101 and free to move in the forward direction, inside the housing 101 to restrict the accidental reverse motion of the needle assembly 102.

The first end (I) of the safety clip 106 is coupled with both the housing 101 and the needle assembly 102, whereas second end (II) of the safety clip 106 is externally coupled with the plunger 105 by using a positive lock. The whole arrangement constitutes the releasable seal means of the present embodiment.

Figure 1C:
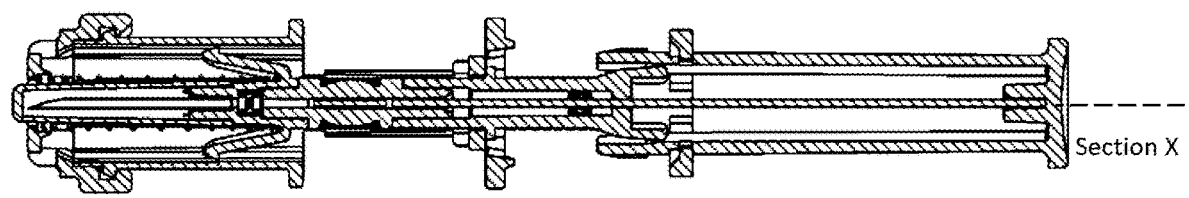
Figure 1C:
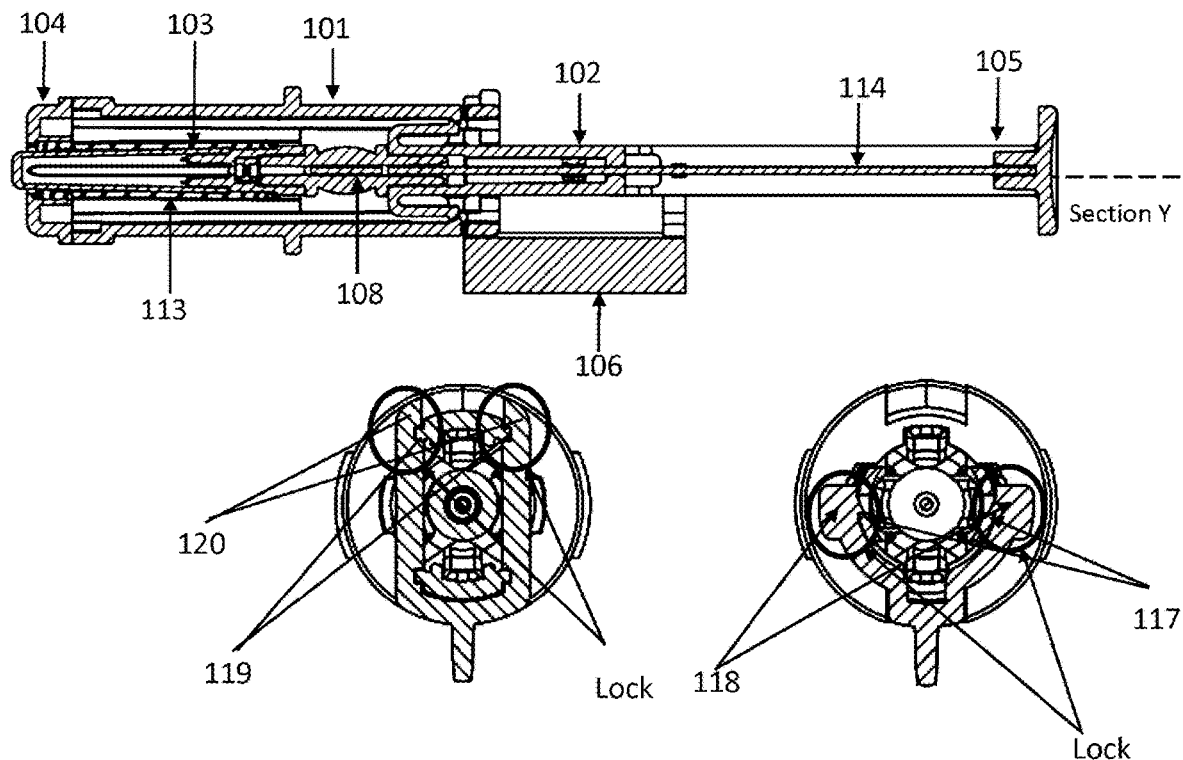
Figure 1C:
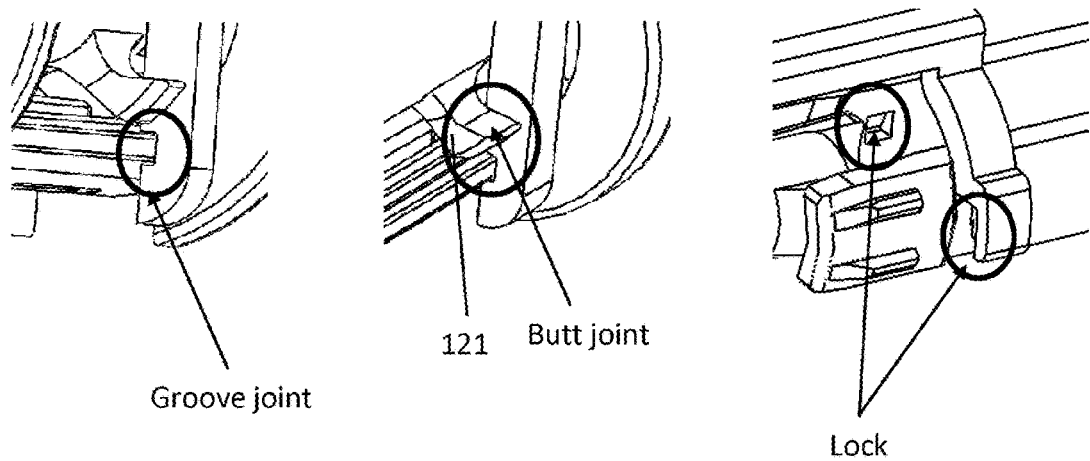

Reference is next invited from the accompanying FIG. 1c, which shows cross sectional view of the present injecting system with push based operable safety housing.

As shown in the accompanying FIGS. 1a, 1b and 1c, the second end (II) of the safety clip 106, which is coupled with the plunger 105 by using the positive lock, includes at least one external opening or slot 117 in the plunger, at proximal end and cooperative protrusion 118 on the second end of safety clip 106, which is configured to be detachably engaged with said opening or slot 117 in the plunger 105.

The first end (I) of the safety clip 106, which is coupled with distal end of the housing 101, includes tongue 119 and groove 120 joint. The first end (I) of the Safety clip 106 includes butt 121 joint to couple with the label holder 107 of the needle assembly 102. The tongue and groove (119, 120) joint between the housing 101 and the safety clip 106 facilitates the safety clip 106 to slides through the housing 101.

The safety lock 106 ensures that, the plunger 105 does not become loose part. The safety clip's butt joint 121 with the label holder 107 of the needle assembly 102 ensures that, the pushing force applied on the plunger 105 gets transferred to the needle assembly 102 via the safety clip 106. This enables cooperative movement of the plunger 105 and the needle assembly 102.

In the initial stage, as shown in the FIG. 1c, the needle assembly 102 with the protective cap 113 covering the cannula 112 is held within the housing 101 under tension of the spring 103. When a force is applied on the plunger 105, the force is transferred to the needle assembly 102 through the safety clip 106, which drives both the plunger 105 and the needle assembly 102 in forward direction within the housing 101. During this driving of the needle assembly 102, the implant 108 does not move independently with respect to the needle assembly 102 as the plunger rod 114 cannot move through the plunger rod guide 110 due to the cooperative movement of the plunger 105 and the needle assembly 102.

Figure 1D:
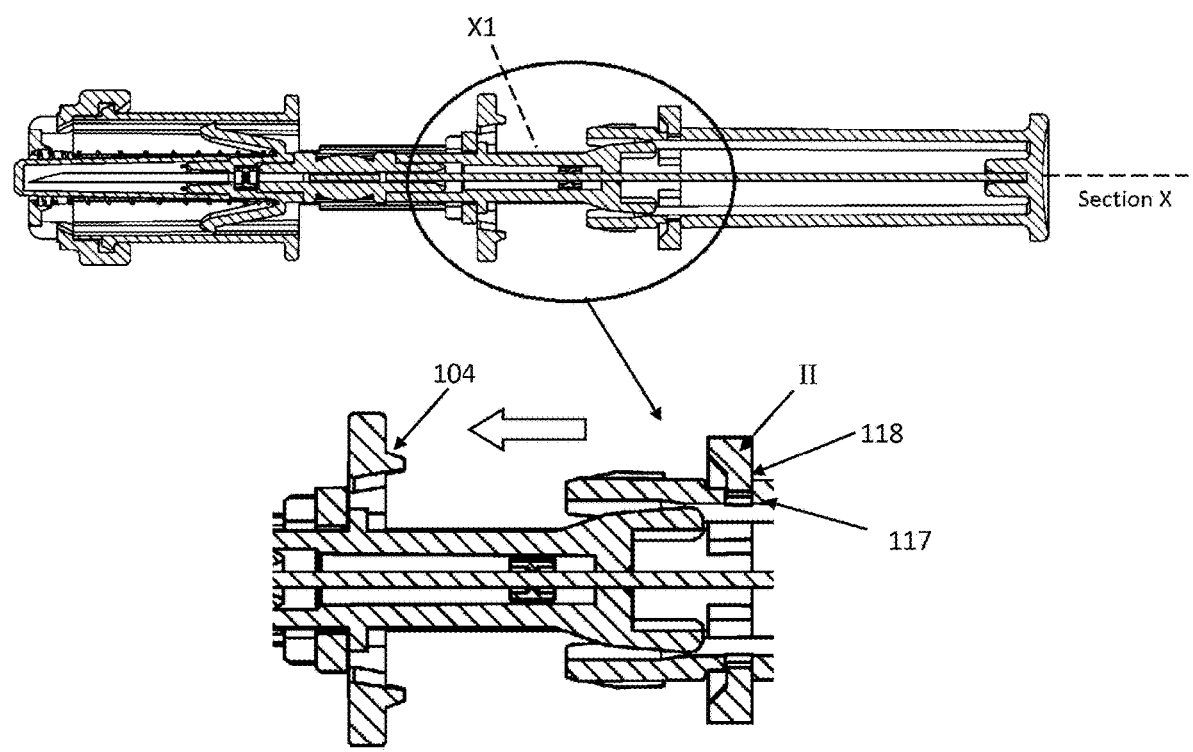

On continued application of the force on the plunger 105, the cannula 112 is completely ejected out along with the protective cap 113 from the housing 101. During this stage, the second end (II) of the safety clip 106 slides into mating protrusion 122 on the housing 101 which widens the second end (II) of the safety clip 106 at point X1 to disengage the positive lock by putting the protrusion 118 out of the slot 117, as shown in the accompanying FIG. 1d. The first end (I) of safety clip 106 slides within the tongue 120 of the housing 101 and gets released at point X3, where the tongue 120 ends to facilitate the removal of safety clip 106. The above arrangement constitutes the seal releasing means of the present embodiment.

A snap lock 123 of the plunger 105 also gets locked within the housing 101 at point X2. The situation is shown in the accompanying FIG. 1e.

At this stage, the spring 103 gets fully compressed and the needle assembly 102 gets locked into the housing top at point X4, as the snap lock 115 of the needle hub 111 is engaged with cooperative locking portion in the housing top 104 with an audible click sound, as shown in the FIG. 1e. This ensures that the forward and reverse movement of the needle assembly 102 is being arrested.

The safety clip 106 is free to be pulled out of the assembly. After, the needle assembly 102 gets locked into the housing 101 with the cannula 112 completely ejected out along with the protective cap 113 from the housing 101, the protective cap 113 is removed as shown in the accompanying FIG. 1f. The needle cannula 112 after removal of the cap 113 can be pierced into the body/tissue by only holding the housing 101.

The removal of the safety clip 106, makes the plunger 101 moveably independent from the needle assembly 102 and further application of force on the plunger 105, which is now independent of the needle assembly, moves the rod 114 in forward direction through the rod guide 110 and push the implant 108 through the cannula 112, into the tissue, as shown in the accompanying FIG. 1g.

At the end of the injection stage, plunger outer body slides over the snap lock of the needle hub 111 at point X4 and at the last point of the plunger movement towards distal end, the plunger front end 124 forces the snap lock 115 of the needle hub 111 to compress and disengage from the lock of the housing top 104 at the point X4, as shown in the FIG. 1h. Herein, the plunger front end 124, which forces the snap lock 115 of the needle hub 111 to compress and disengage from the lock of the housing top 104, acts as the first disengagement means of the present embodiment.

When the snap lock 115 of needle assembly is disengaged from the housing 101, the compressed spring 103 gets expanded and drives the needle assembly 102 in backward direction resulting retraction of the cannula 112 from the skin automatically along with the plunger. The needle assembly 102 with the cannula 112 then gets secured inside the housing 101. During the needle retraction from the skin, the plunger is also retracted back as it has an engagement with the needle assembly at point X4.

Figure 1I:
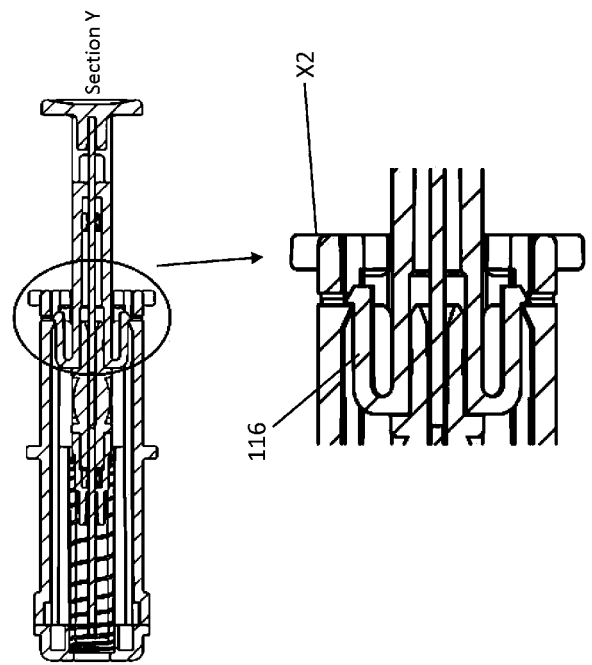

At the end of the retraction stage, label holder of the needle assembly gets snap locked with the housing at Point X2, as shown in the accompanying FIG. 1i. This constitutes the second engagement means of the present embodiment. After retraction stage, the needle assembly 102 is permanently arrested inside the housing 101, thus rendering the needle assembly useless & can only be disposed off.

In this stage, the plunger will not be able to push the needle assembly in forward direction as it is locked at point X2 within the housing. The Plunger has a freedom to move only backward which anyway is harmless to user/Patient.

Figure 2A:
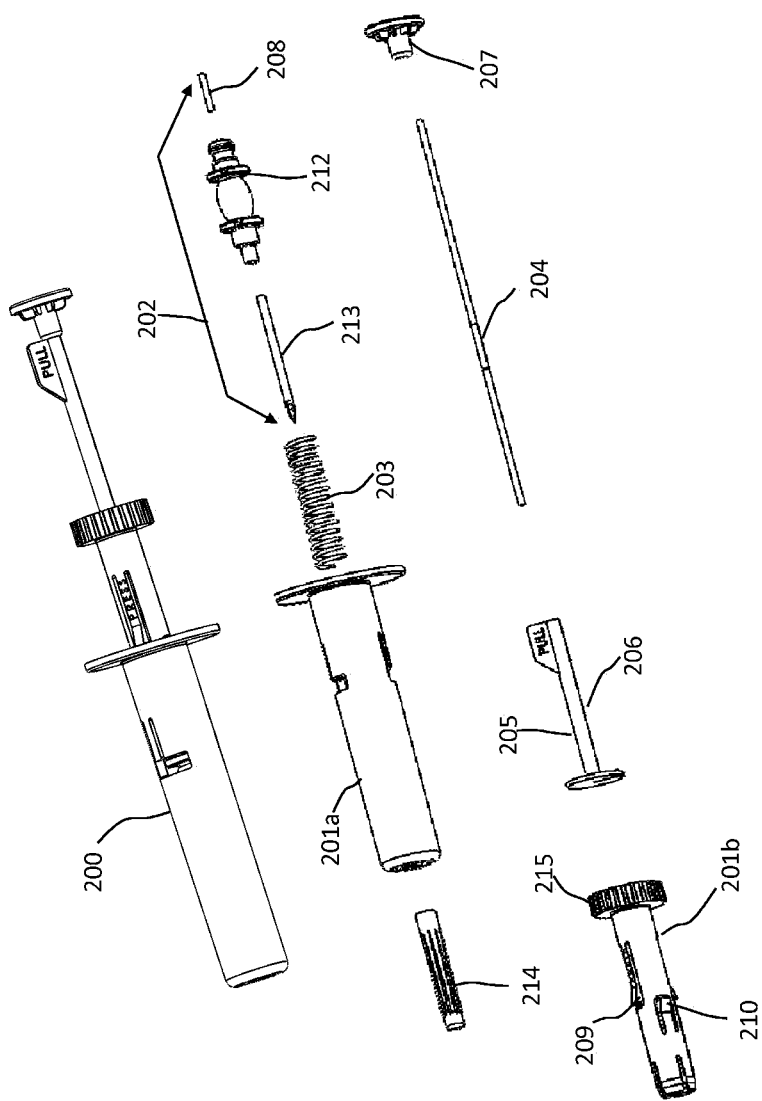
Figure 2B:
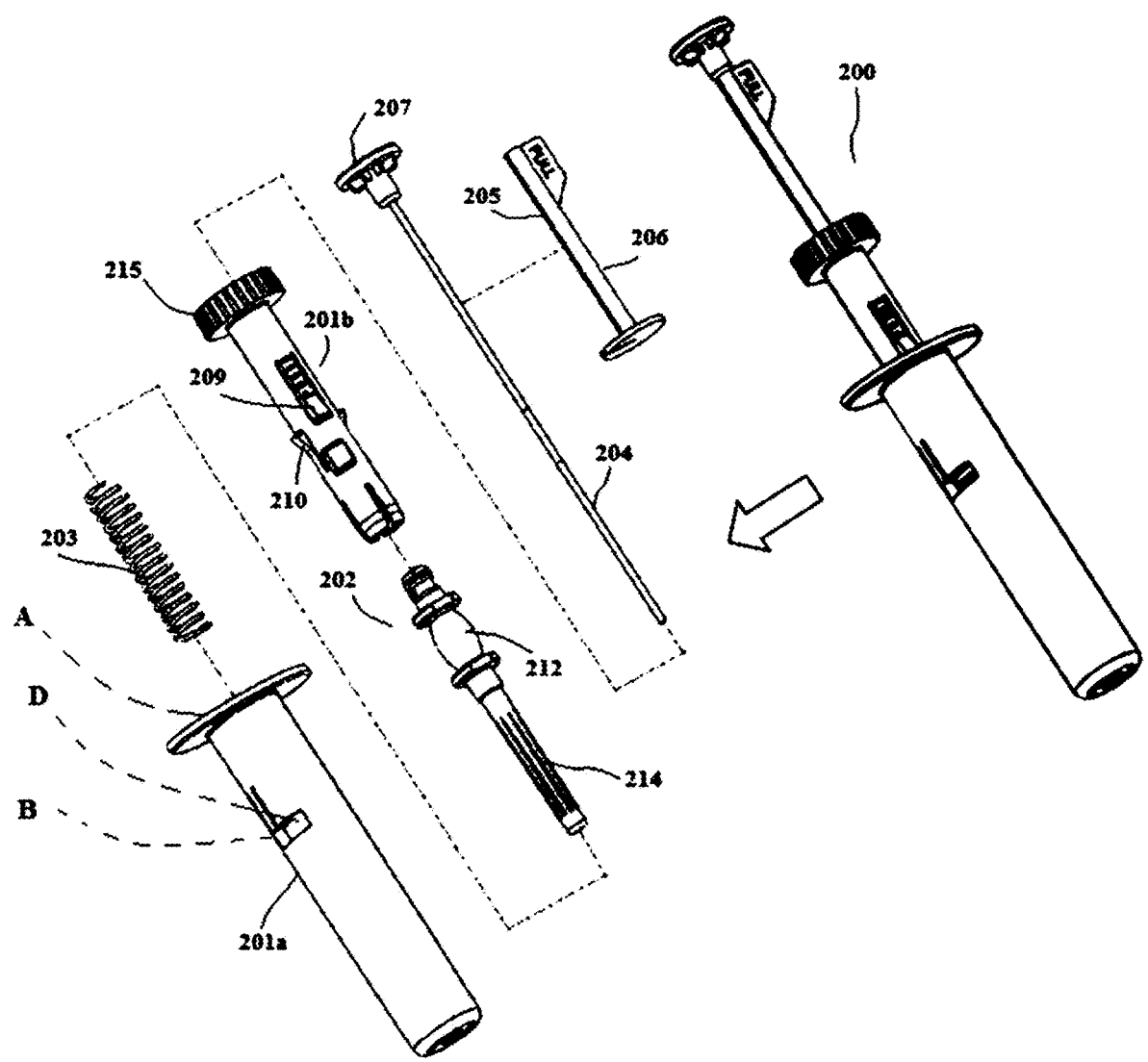

Reference is next invited from the accompanying FIGS. 2a and 2b which shows a preferred embodiment of the present injecting system with a twist based safety housing. As shown in the referred figures, the twist based prefilled medicament injecting device 200 includes a needle assembly 202 and an enclosing means. The enclosing means is divided in two parts viz. an outer housing 201a and an inner housing 201b. The outer housing 201a fully enclose the needle assembly 202. The inner housing 201b is coupled to a distal end of the outer housing 201a. The inner housing 201b telescopically moves within the outer housing 201a.

The needle assembly 202 is disposed within the outer housing 201a under biasing support of a spring 203. A back end of the needle assembly 202 is coupled to a plunger rod 204 by a supportive safety cap 206. A plunger cap 207 is provided at a back end of the plunger rod 204. The coupling point between the plunger rod 204 and the back end of the needle assembly 202 is surrounded by the inner housing 201b.

One end of the safety cap 206 is locked inside the inner housing 201b by a butt joint. The other end of the safety cap 206 is coupled to the plunger cap 207 by a butt joint. The safety cap 206 includes a slot or opening 205 running through its length to ensure engagement of the safety cap 207 with the plunger rod 204.

The lock between the safety cap 206 and the inner housing 201b is shown in the accompanying FIG. 2c. This lock ensures that the plunger rod 204 does not become a loose part. The butt joint between the safety cap 206 and the plunger cap 207 ensures that the plunger rod 204 does not move independently with respect to the inner housing 201b. This butt joint also ensures that, a needle ejecting force applied on the plunger cap 207 is transferred to the inner housing 201b and the needle assembly 202 via the safety cap 206.

The inner housing 201b includes a forward snap 209 on external surface of the inner housing 201b to ensure that the needle assembly 202 does not move forward. The inner housing 201b also includes a reverse snap 210. The reverse snap 210 is seated inside a groove of the outer housing 201a to arrest any rotation of the inner housing 201b during the needle ejection stage.

The outer housing 201a includes a forward snap 211. This forward snap 211 holds the needle assembly against the spring at Point B.

The needle assembly 202 includes a cannula 213 at a front end of the needle assembly and a subsequent needle holder 212. The cannula 213 has a fluid communicable connection with the needle holder 212. The needle holder 212 is prefilled with implant or the injectable substances 208.

The plunger rod 204 can move through the needle holder 212 and push the implant or the injectable substances 208 in forward direction into the cannula 213. The cannula 213 is adapted to eject through a small opening in the outer housing 201a and penetrate a body or tissue to deliver the implant or the injectable substances. A protective cap 214 is provided on the cannula 213.

Initially, as shown in the FIG. 2c, the needle assembly 202 with the cannula 213 covered by the protective cap 214 is held within the outer housing 201a under bias of the spring 203. To eject the cannula 213 out of the outer housing 201a, the lock at Point A is released by pressing the forward snap 209 down. After releasing the lock at Point A, a pushing force applied on the plunger cap 207 is transferred to the needle assembly 202 through the safety cap 206 which drives the needle assembly 202, the inner housing 201b in forward direction through the outer housing 201a. During this movement of the needle assembly 202, the implant 208 does not move as the plunger rod 204 cannot move through the needle holder 212 due to the safety cap 206 based coupling of the plunger rod 204 with the needle assembly 202. In this embodiment the safety cap acts as the releasable seal means.

On application of the pushing force on the plunger cap 207, the cannula 213 covered with the protective cap 214 is completely ejected from the outer housing 201a. In this stage, as shown in the FIGS. 2d and 2e, the reverse snap 210 of the inner housing 201b is moved forward within the tongue and grove joint and gets locked with the forward snap lock 211 in the outer housing 201a at Point B. This causes an audible click sound. The spring 203 gets fully compressed in this stage and the needle assembly 202 is engaged with the outer housing 201a at Point B which arrest the reverse movement of needle assembly 202. The forward movement of the needle assembly 202 is also arrested by a butt joint between the inner and the outer housing. The combination of the reverse snap 210 and the forward snap lock 211 act as the first engagement means. The stressed forward snap 209 of the inner housing at Point C rides within the inner surface of the outer housing (FIG. 2d). In this stage, the safety cap 206 can be pulled out from the assembly to disengaged the plunger rod 204 from the needle assembly 202. The safety cap 206 here performs as the seal releasing means. The protective cap 214 is removed, as shown in the accompanying FIG. 2f, for exposing the cannula 213 and piercing into a body/tissue.

Now, further application of the pushing force on the plunger cap 207, moves the plunger rod 204 in forward direction into the needle holder which push the implant 208 through the cannula 213, into the tissue, as shown in the accompanying FIG. 2g. At the end of the injection stage, the plunger cap 207 sits within the inner housing pocket and it cannot be taken out by hand.

At the end of the injection stage, to withdraw the cannula from the skin, the inner housing needs is rotated by holding the grip area 215 in counter clockwise direction. The present embodiment includes a circular snap 218 between the needle assembly and the outer housing which acts as the first disengagement means for disengaging the needle assembly from the outer housing.

Figure 2H:
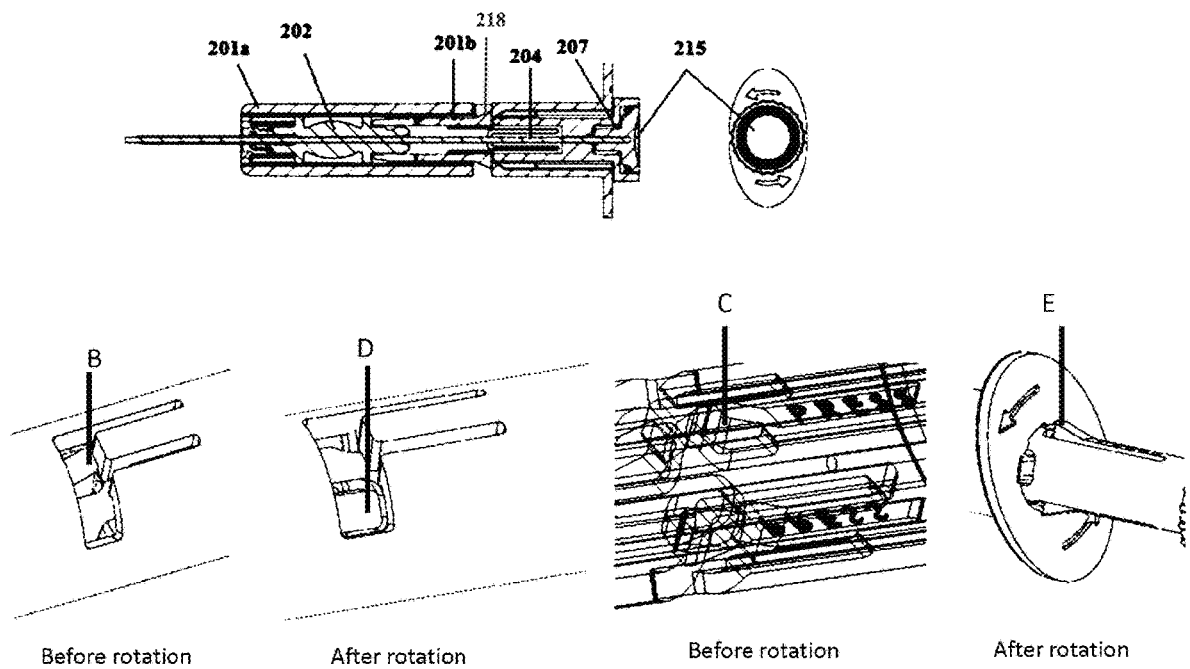

As shown in the accompanying FIG. 2h, when the inner housing 201b is rotated, the plunger rod 204 and the cap 207 also rotate but the needle assembly 202 will not rotate due to the rotation arresting circular snap 218 lock between the needle assembly 202 and the outer housing 201a. The rotation of inner housing 201b, the plunger rod and the plunger cap with respect to the outer housing 201a disengages the lock of the reverse snap 210 at Point B and the reverse snap 210 reaches to the Point D at outer housing 201a. The stressed forward snap 209 of the inner housing 201b at Point C which rides within the inner surface of the outer housing 201a stays at Point E.

Figure 2I:
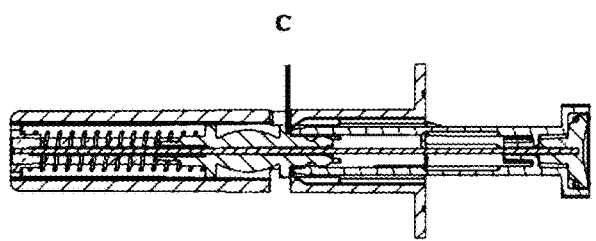

When the inner housing 201b is disengaged from the outer housing 201a, the spring 203 gets expanded and moves the needle assembly in backward direction along with the plunger withdrawing the cannula 213 from the skin. The needle assembly gets secured inside the outer housing. At the end of the backward movement stage, the second engagement means which includes a lock between the needle holder and the forward snap lock permanently arrests the needle assembly in the outer housing at point C as shown in FIG. 2i, thus rendering the syringe use less. The plunger will not push the needle assembly forward, as it is locked at point E on the outer housing.

Figure 3B:
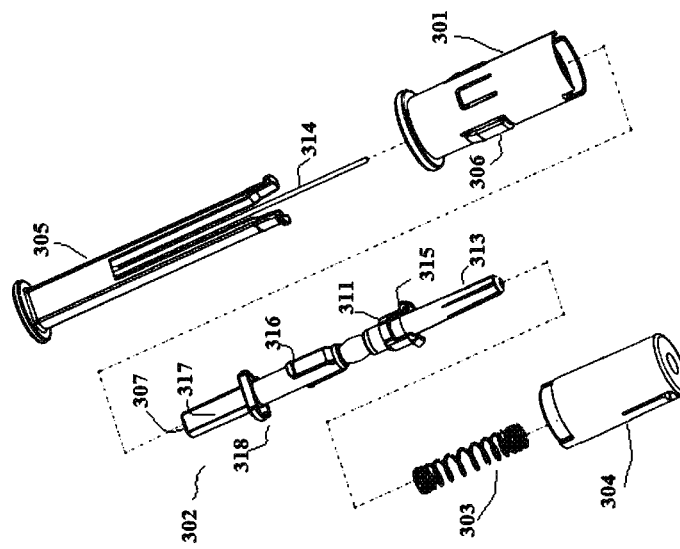
Figure 3A:
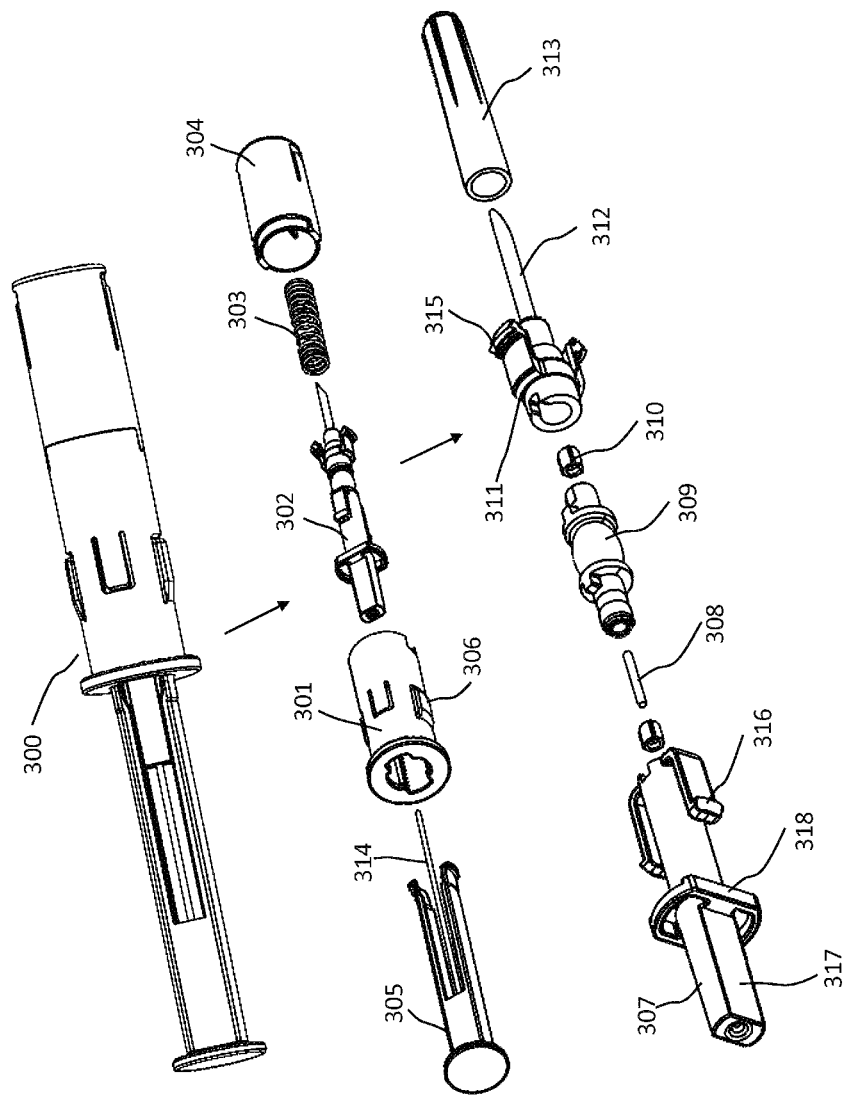

Reference is next invited from the accompanying FIGS. 3a and 3b which show a preferred embodiment of the present injecting system with press based operable safety housing. As shown in the referred figures, injecting system 300 includes a needle assembly 302 which is fully enclosed within a housing 301 preferably a cylindrical barrel. The needle assembly 302 is secured within the housing 301 support of a spring 303 positioned between housing top 304 and front end of the needle assembly 302. Back end of the needle assembly 302 is coupled with a plunger 305 with an insert molded rod 314. A press button 306 is provided on the housing 301 at a selected position between the proximal and distal end of the housing 301.

The needle assembly 302 includes a label holder 307 at its back end, a plunger rod guide 310 running through an implant container cum magnifier 309 and positioned in an axially symmetric manner between the label holder 307 and a needle hub 311. The plunger rod 314 can move through the plunger rod guide 310 and push implant/medicament or the injectable substances 308 which are prefilled within the plunger rod guide 310 towards the needle hub 311. The needle hub 311 houses a cannula 312 having fluid communicable connection with the plunger rod guide 310 to receive the implant or the injectable substances 308. The cannula 312 is adapted to penetrate within the body or tissue and deliver the implant or the injectable substances 308. A protective cap 313 is provided on the cannula 312.

The needle hub 311 includes snap lock 315 which is configured to engage with cooperative locking portion in the housing top 304 and act as the first engagement means. The label holder 307 includes a snap lock 316 which sits within the housing 301 and free to move in the forward direction, inside the housing 301.

Back end of the label holder 307 includes across flat surface 317 which is configured to engage with inner surface of the housing 301 to arrest any rotational movement of the needle assembly 302 with respect to the housing 301 and allow only spring biased forward and backward motion of the needle assembly 302 within the housing 301.

Figure 3C:
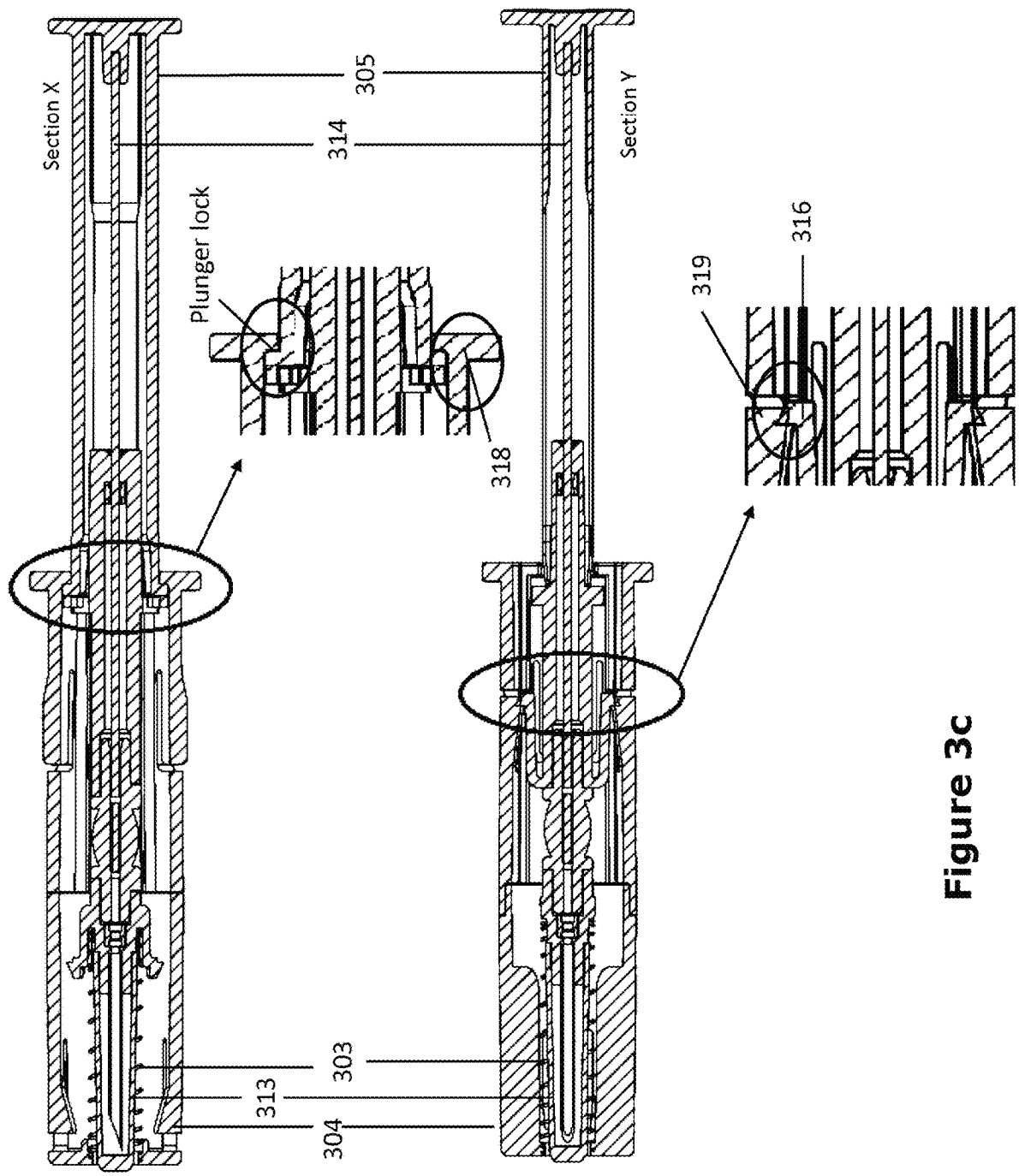

Reference is next invited from the accompanying FIG. 3c which shows cross sectional views of the present injecting system with press based operable safety housing along with engagement mechanism between the housing 301, the needle assembly 302 and the plunger 305.

As shown in the accompanying FIGS. 3a, 3b, 3c, the plunger 305 is irremovably secured inside the housing 301 and the plunger outer body is coupled with the with the label holder 318 of the needle assembly 302 by using a butt joint 318 which ensures that the pushing force applied on the plunger 305 gets transferred to the needle assembly 302 via the butt joint 318 and causing cooperative movement of the needle assembly 302 and the plunger 305. The butt joint acts as the releasable seal means.

In the initial stage, the needle assembly 302 with the protective cap 313 covering the cannula 312 is held within the housing 301 under tension of the spring 303. The snap lock 316 of the label holder 307 is held just above its cooperative mating snap portion 319 in the housing 301.

When a Force is applied on the plunger 305, the force is transferred to the needle assembly 302 through the butt joint 318 in the label holder of the needle assembly 302 which drives the needle assembly 302 inside the housing 301 in forward direction. During this driving of the needle assembly 302, the implant 308 does not move independently with respect to the needle assembly 302 as the plunger rod 314 cannot move through the plunger rod guide 310 due to the butt joint 318 supported cooperative movement of the plunger 305 and the needle assembly 302.

Figure 3D:
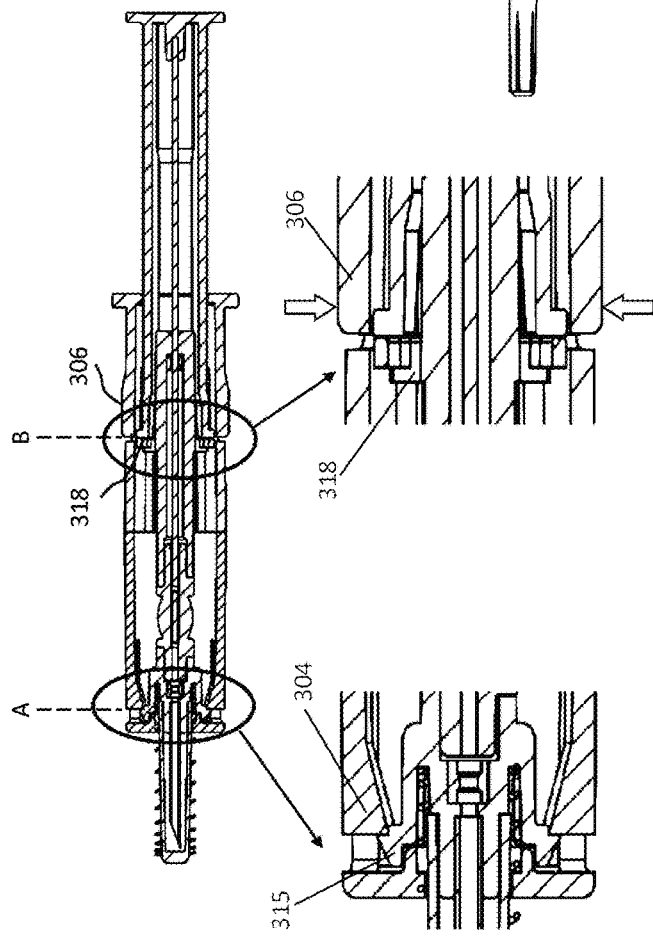

With the continued application of force on the plunger 305, the cannula 312 is completely ejected out along with the protective cap 313 from the housing 301. During this stage, the spring 303 gets fully compressed and the needle assembly gets engaged with the housing at point A, as the snap lock 315 of the needle hub 311 is engaged with cooperative locking portion in the housing top 304 with an audible click sound, as shown in the FIG. 3d. This ensures that the forward and reverse movement of the needle assembly 302 is arrested. The front end 319 of plunger outer body which is coupled with the needle assembly 302 at the butt joint 318 reaches the region of Press button 306 on the housing 301 at point 'B'. The press button act as the seal releasing means.

Figure 3E:
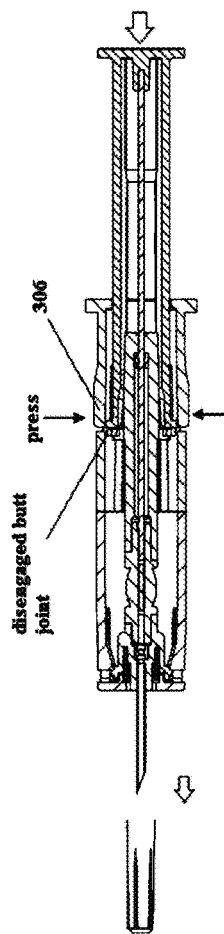

After, the needle assembly 302 gets engaged with the housing top 304 with the cannula 312 is completely ejected out along with the protective cap 313 from the housing 301, the protective cap 313 is removed as shown in the accompanying FIG. 3e. The needle cannula 312, after removal of the cap, can be pierced into the body/tissue by only holding the housing. Now, application of a gentle force on the press button 306 on the housing 301 disengages the butt joint 318 based engaged disposition between the needle assembly and the plunger 305.

Figure 3F:
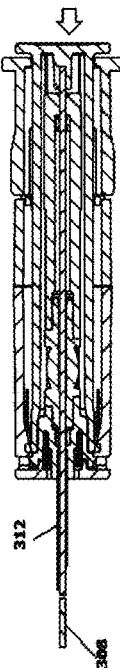

Now further application of force on the plunger 305, the plunger body, which is now independent of the needle assembly due to disengagement of the Butt joint 318 between needle assembly and the plunger front end, moves in forward direction and push the rod 314 through the rod guide 310 and deliver the implant/medicament 308 through the cannula 312, into the tissue as shown in the accompanying FIG. 3f.

At the end of the injection stage, plunger outer body slides over the snap locking feature of the needle hub 311 at point A and at the last point of the plunger movement towards distal end, the plunger front end forces the snap lock 315 of the needle hub 311 to compress and disengage from the lock of the housing top 304 at the point A. Herein the plunger front end act as the first disengagement means.

When the snap lock 315 of needle assembly is disengaged from the housing 301, the compressed spring 303 gets expanded which moves the needle assembly 302 in backward direction to retract the cannula 312 from the skin automatically along with the plunger 305. During the needle retraction from the skin, the plunger 305 is also retracted back as the plunger portion inside the housing has an engagement with the needle assembly 302.

At the end of the retraction stage, the label holder 307 in the needle assembly gets snap locked with the housing at Point C as shown in the accompanying FIG. 3h. In this retraction stage, the needle assembly 302 is permanently arrested inside the housing, thus rendering the syringe use less & can only be disposed off. The Plunger 305 has a freedom to move only backward which anyway is harmless to user/Patient. Herein, the snap lock 316 on the label holder act as the second engagement means.

Figure 4A:
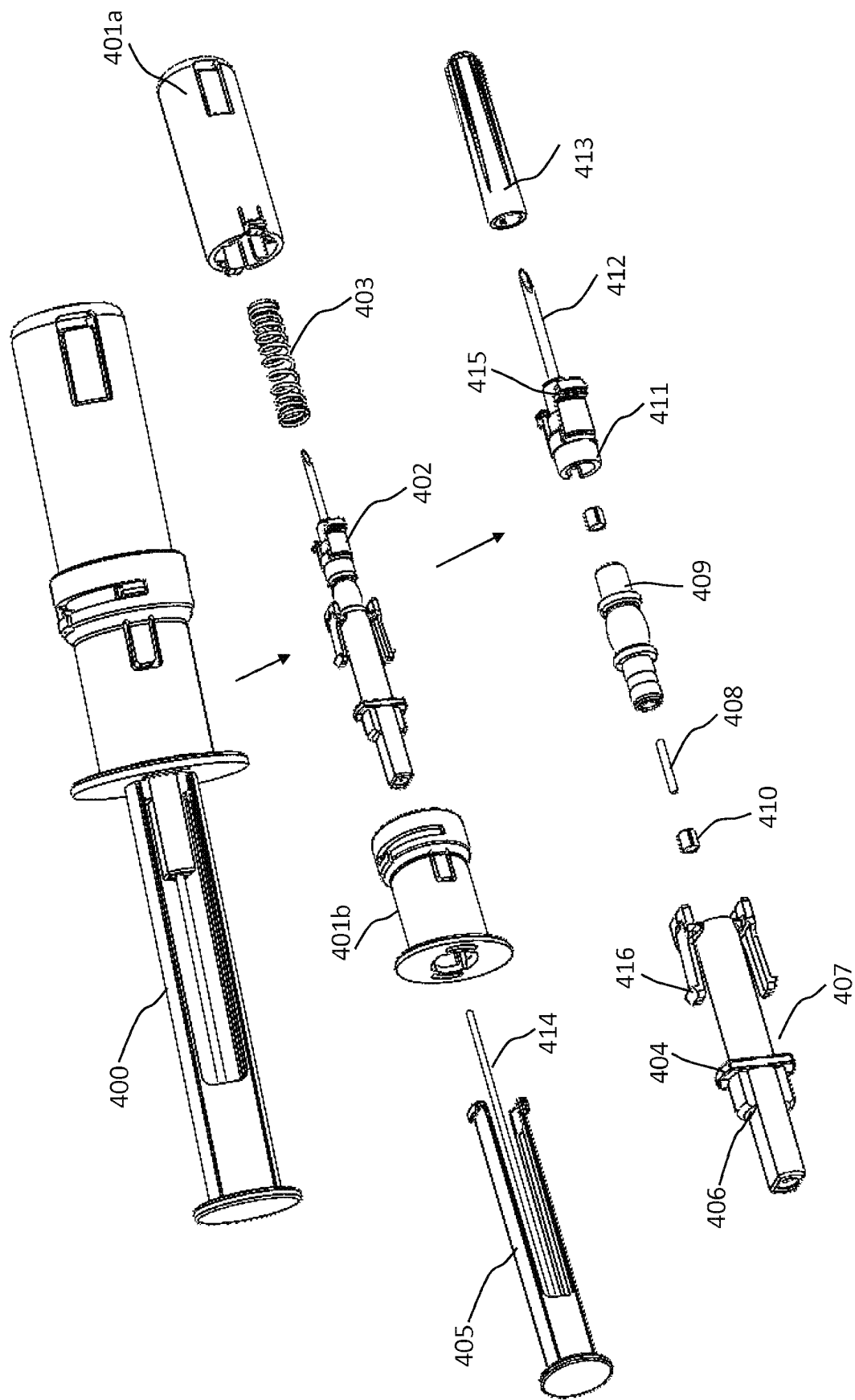
Figure 4B:
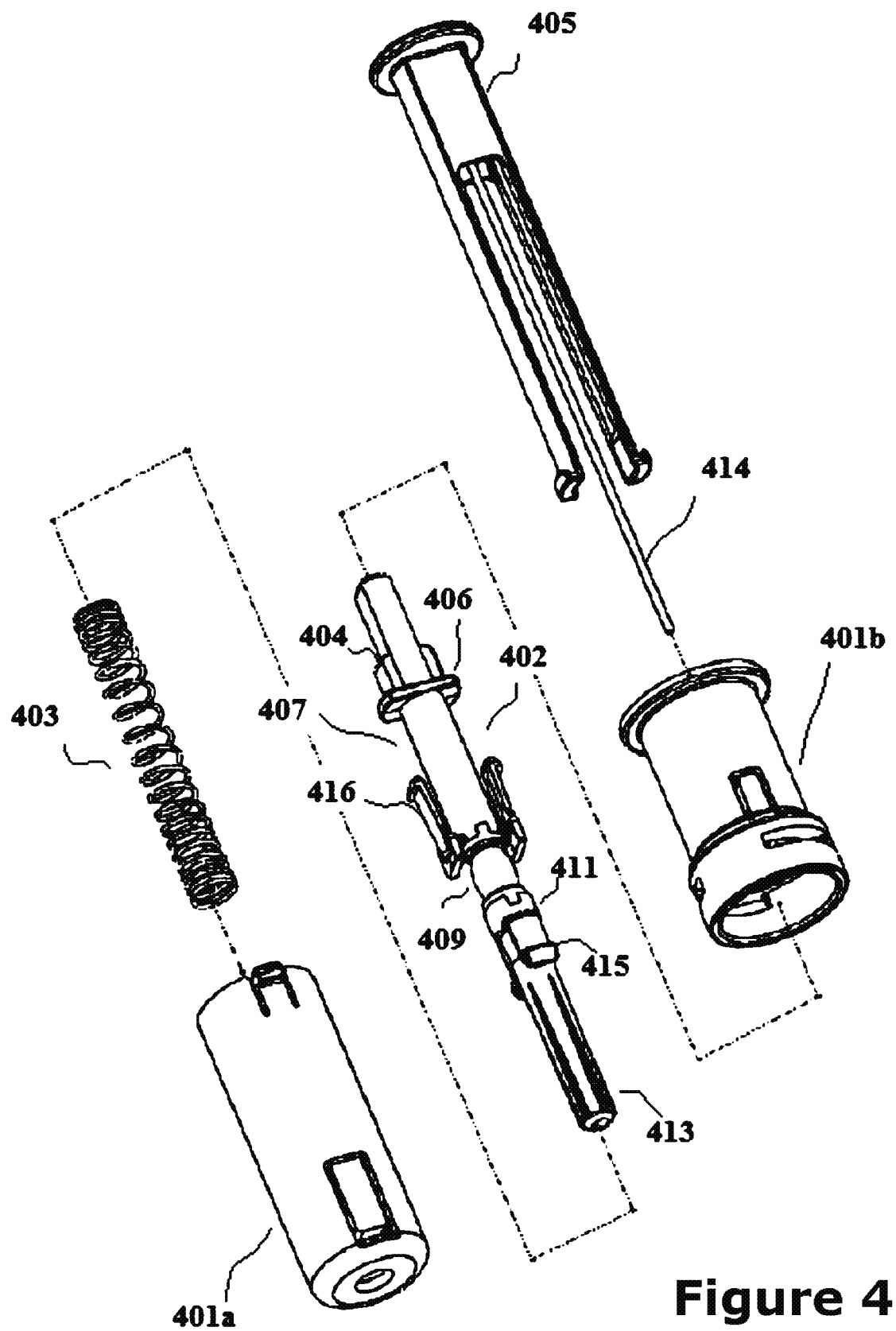

Reference is next invited from the accompanying FIGS. 4a and 4b which are showing a preferred embodiment of the present prefilled medicament injecting device with hybrid safety housing. As shown in the referred figures the hybrid prefilled medicament injecting device 400 includes a needle assembly 402 which is fully enclosed within a housing. The housing is comprising of a top housing 401a and a bottom housing 401b. The top bottom housings 401a & 401b are axially coupled to each other.

The needle assembly 402 is secured within the housing 401a & 401b and supported by spring 403. The spring is positioned between the top housing 401a and front end of the needle assembly 402. Back end of the needle assembly 402 is coupled with a plunger 405. The plunger 405 includes an insert molded rod 414.

The needle assembly 402 includes a label holder 407 at its back end, a needle hub 411 at its front end, and a plunger rod guide 410. The plunger rod guide 410 is running through an implant container cum container 409 and positioned between the label holder 407 and the needle hub 411 in an axially symmetric manner. The plunger rod 414 is configured to move through the plunger rod guide 410 and push implant/medicament or the injectable substances 408 in the plunger rod guide 410 towards the needle hub 411. The needle hub 411 houses a cannula 412 which has a fluid communicable connection with the plunger rod guide 410 to receive the implant or the injectable substances 408. The cannula 412 is adapted to penetrate within the body or tissue and deliver the implant or the injectable substances 408. A protective cap 413 is provided on the cannula 412.

The needle hub 411 includes a snap lock 415 which acts as the first engagement means. The snap lock 415 is configured to engage with cooperative top locking portion in the top housing 401a. The label holder 407 includes a snap lock 416, which can sits within the housings 401a and 401b and free to move in the forward direction.

Back end of the label holder 407 includes a lateral flat surface 406. The lateral flat surface 406 is configured to selectively engage with inner surface of the housings to selectively arrest any rotational movement of the needle assembly 402 with respect to the housings. The lateral flat surface 406 allow only spring biased forward and backward motion of the needle assembly 402 within the housings.

Figure 4C:
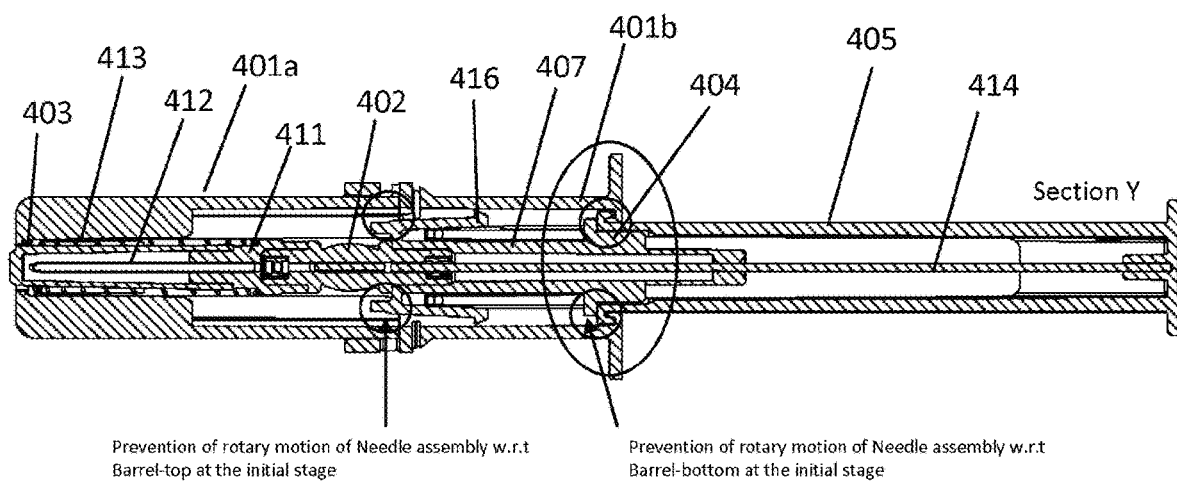

Reference is next invited from the accompanying FIGS. 4c and 4d which are showing cross-sectional view of the present prefilled medicament injecting device with engagement mechanism between the housings, the needle assembly 402 and the plunger 405.

As shown in the accompanying FIGS. 4a, 4b, 4c, 4d, the plunger 405 is irremovably secured inside the bottom housing 401b and the plunger outer body is coupled with the with the needle assembly 402 by a butt joint 404 on the label holder 407. This coupling acts as the releasable seal means and ensures that the pushing force applied on the plunger 405 gets transferred to the needle assembly 402 via the butt joint 404. This causes cooperative movement of the needle assembly 402 and the plunger 405.

In the initial stage, front portion of the needle assembly 402 is enclosed by the top housing 401a and back portion of the needle assembly 402 is enclosed by the bottom housing 401b. In this stage, rotation of the needle assembly 402 with respect to the top housing 401a and the bottom housing 401b is arrested by the locking surface. More specifically, in his stage, rotational movement of the bottom housing 401b w.r.t. the top housing 401a is arrested by lateral flat surface 406 engagement of the needle assembly 402 with inner surface of the top housing 401a and lateral flat surface 406 engagement of the needle assembly 402 with inner surface of the bottom housing 401b. The rotational movement of the plunger w.r.t the bottom housing 401b is arrested by lateral flat surface engagement of the Plunger with the bottom housing.

When a Force is applied on the plunger 405, the force is transferred to the needle assembly 402 through the butt joint 404. This drives the needle assembly 402 inside the housing in forward direction. During this forward motion of the needle assembly 402, the implant 408 does not move, as the plunger rod 414 cannot move through the plunger rod guide 410 due to the butt joint 404 supported cooperative movement of the plunger 405 and the needle assembly 402.

Continuing application of the force on the plunger 405, enables the cannula 412 to completely ejected out along with the protective cap 413 from the housing. During this stage, as shown in the FIG. 4e the spring 403 gets fully compressed and the needle assembly is engaged with front of the top housing 401a at point A, as the snap lock 415 of the needle hub 411 is engaged with cooperative locking portion in the front of the top housing 401a with an audible click sound. This engagement arrests the forward and reverse movements of the needle assembly 402. Front end of plunger outer body, which is coupled with the needle assembly 402 at the butt joint 404, reaches at point 'B', where joining surface between the top and the bottom housings lies with lateral flat surface releasing gap in housing inner surfaces. This lateral flat surface releasing gap acts as the seal resealing means (FIG. 4e).

In the lateral flat surface releasing gap, the surface engagement between needle assembly 404 and the bottom housing 401b is released, permitting rotation of the top housing 401a and the needle assembly 402 w.r.t the bottom housing 401b.

Now, holding the top housing 401a, a rotation of the bottom housing 401b in 90° clockwise direction will disengage the butt joint 404 between the plunger 405 and needle assembly 404 with an audible click sound. During this rotation, the needle assembly 402 which is coupled to the top housing 401a does not rotate, but the bottom housing and the plunger 405 rotate 90° w.r.t the needle assembly 402, due to the lateral flat engagement of plunger with the bottom housing 401a. A lock feature is provided in the bottom housing 401b to restrict rotation in CCW direction once it is rotated in CW direction.

After, the needle assembly 402 is engaged with the top housing 401a, and the cannula 412 is completely ejected out along with the protective cap 413 from the housing, the protective cap 413 is removed, as shown in the accompanying FIG. 4f.

The needle cannula 412, after removal of the cap, is pierced into the body/tissue by only holding the housing. In this stage, further application of the force on the plunger 405, the plunger body, which is disengaged from the needle assembly 402, moves in forward direction and push the rod 414 through the rod guide 410 to deliver the implant 408 through the cannula 412, into the tissue, as shown in the accompanying FIG. 4g.

At the end of the injection stage, plunger outer body slides over the snap locking feature of the needle hub 411 (at point A) and the plunger front end forces the snap lock 415 to compress and disengage from the lock with the front of the top housing top. Herein, the plunger outer body act as the first disengagement means.

When the snap lock 415 of needle assembly is being disengaged from the housing 401, the compressed spring 403 gets expanded and moves the needle assembly 402 in backward direction to retract the cannula 412 from the skin automatically along with the plunger 405. During the needle retraction from the skin, the plunger 405 is also retracted back, as the plunger portion inside the housing has an engagement with the needle assembly 402.

Figure 4H:
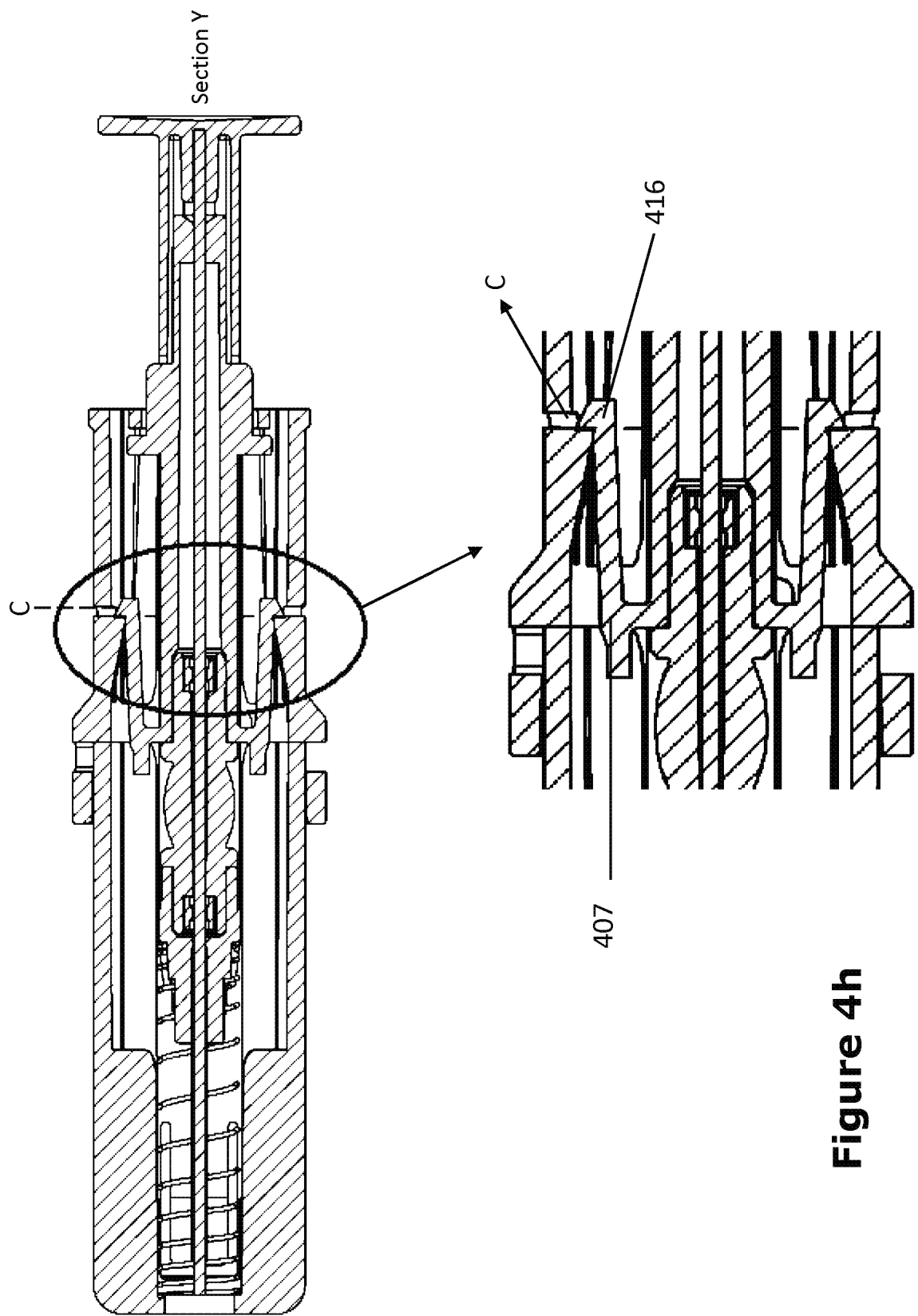

At the end of the retraction stage, the label holder 407 in the needle assembly gets snap locked with the housing (at Point C as shown in the accompanying FIG. 4h). Herein, the snap lock of the label holder 407 acts as the second engagement means. In this stage, the Needle assembly 402 is permanently arrested inside the housing, thus rendering the syringe use less.

The invention claimed is:

1. A safety housing based implant/medicament injecting system comprising:
   a housing comprising an outer housing and an inner housing;
   a needle assembly having a cannula at a front end of the needle assembly and a subsequent needle holder that is in fluid communicable connection with the cannula, the needle holder being fully accommodated within the inner housing and the outer housing and supported with a spring positioned between an outer housing top and the front end of the needle assembly;
   a plunger rod configured for:
   an initial forward motion of the plunger rod to eject the cannula through an opening in the outer housing, wherein a releasable seal means operatively couples the plunger rod with a back end of the needle assembly and with the inner housing, and wherein a first engagement means engages the needle assembly with the outer housing at an end of the initial forward motion of the plunger rod; and
   a subsequent continuing forward motion of the plunger rod to inject an implant/medicament through the ejected cannula, wherein a seal releasing means disengages the coupling between the needle assembly, the inner housing and the plunger rod;
   a first disengagement means for disengaging the first engagement means; and
   a second engagement means on the needle holder to permanently arrest the needle assembly in the housing after use.

2. The safety housing based implant/medicament injecting system as claimed in claim 1, wherein the outer housing is configured to fully enclose the needle assembly, the inner housing is coupled to a back end of the outer housing and is configured to telescopically move within the outer housing, and said inner housing surrounds a coupling point between the plunger rod and the back end of the needle assembly.

3. The safety housing based implant/medicament injecting system as claimed in claim 1, wherein the plunger rod includes a plunger cap at a back end of the plunger rod.

4. The safety housing based implant/medicament injecting system as claimed in claim 3, wherein the releasable seal means involves a safety cap provided on the plunger rod and providing a butt joint with the inner housing;
   wherein the safety cap ensures that the plunger rod cooperatively moves with the inner housing and the needle assembly and that any pushing force applied on the plunger cap gets transferred to the inner housing and the needle assembly via the safety cap so that the needle assembly, which is surrounded with the inner housing, is driven in a forward direction through the outer housing; and
   wherein said cooperative movement of the plunger rod with the inner housing and the needle assembly restricts plunger rod movement through the needle holder and thus prevents movement of the implant/medicament independently with respect to the needle assembly during the initial forward motion of the plunger rod.

5. The safety housing based implant/medicament injecting system as claimed in claim 3, wherein the needle assembly includes a protective cap on the cannula;
   wherein the first engagement means includes a reverse snap on the inner housing and a forward snap lock in the outer housing;
   wherein, during the initial forward motion of the plunger rod, force is applied on the plunger cap to drive the needle assembly and the inner housing within the outer housing towards the opening in the outer housing; and
   wherein said reverse snap on the inner housing gets snap-locked with the forward snap lock in the outer housing when the cannula and the protective cap are completely ejected through the opening in the outer housing.

6. The safety housing based implant/medicament injecting system as claimed in claim 5, wherein the reverse snap on the inner housing getting snap-locked with the forward snap lock in the outer housing causes an audible click sound and causes the spring to be compressed to arrest reverse movement of the needle assembly with respect to the housing.

7. The safety housing based implant/medicament injecting system as claimed in claim 5, wherein forward movement of the needle assembly when the cannula is completely ejected through the opening in the outer housing is arrested by having a butt joint between the inner housing and the outer housing, and wherein the cannula being completely ejected through the opening allows for the cannula, after removal of the protective cap, to pierce a body, skin or tissue.

8. The safety housing based implant/medicament injecting system as claimed in claim 5, wherein the first disengagement means includes a circular snap between the needle assembly and the outer housing;
   wherein said circular snap enables integrated rotation of the inner housing, the plunger rod and the plunger cap with rotation of a grip area on the inner housing and arrests rotation of the needle assembly;
   wherein said rotation of the inner housing, the plunger rod and the plunger cap disengages the snap-lock between the reverse snap on the inner housing and the forward snap lock in the outer housing; and
   wherein, after the first engagement means is disengaged, the needle assembly automatically retracts within the housing by expansion of the spring.

9. The safety housing based implant/medicament injecting system as claimed in claim 5, wherein the second engagement means includes a lock between the needle holder and the forward snap lock to permanently arrest the needle assembly in the outer housing after use.

10. The safety housing based implant/medicament injecting system as claimed in claim 3, wherein the seal releasing means is in a back end of the inner housing and is a safety cap that can be removed to enable the plunger rod to move independent of the needle assembly when a pushing force is applied on the plunger cap so that the subsequent continuing forward motion of the plunger rod causes the plunger rod to travel in a forward direction through the needle holder and push the implant/medicament through the cannula into tissue.

11. The safety housing based implant/medicament injecting system as claimed in claim 3, wherein at an end of the injection of the implant/medicament, the plunger cap irrecoverably sits within an inner housing pocket.

12. The safety housing based implant/medicament injecting system as claimed in claim 1, wherein the inner housing comprises a reverse snap seated inside a groove of the outer housing to arrest any rotation of the inner housing during the ejection of the cannula from the outer housing.

13. The safety housing based implant/medicament injecting system as claimed in claim 1, wherein the inner housing includes a forward snap configured to be released by pressing, such release causing the inner housing to be driven into the outer housing to eject the cannula out of the outer housing during the initial forward motion of the plunger rod.

\* \* \* \* \*